United States Patent
Bandur et al.

(10) Patent No.: US 9,334,238 B2
(45) Date of Patent: May 10, 2016

(54) N-SUBSTITUTED PYRIDINYLIDENES FOR COMBATING ANIMAL PESTS

(71) Applicant: BASF SE, Ludwigshafen (DE)

(72) Inventors: Nina Gertrud Bandur, Mannheim (DE); Ralph Paulini, Bad Durkheim (DE); Florian Kaiser, Mannheim (DE); Arun Narine, Mannheim (DE); Joachim Dickhaut, Heidelberg (DE); Karsten Körber, Eppelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/389,125

(22) PCT Filed: Mar. 27, 2013

(86) PCT No.: PCT/EP2013/056540
§ 371 (c)(1),
(2) Date: Sep. 29, 2014

(87) PCT Pub. No.: WO2013/144213
PCT Pub. Date: Oct. 3, 2013

(65) Prior Publication Data
US 2015/0057280 A1 Feb. 26, 2015

Related U.S. Application Data

(60) Provisional application No. 61/617,706, filed on Mar. 30, 2012, provisional application No. 61/731,515, filed on Nov. 30, 2012.

(30) Foreign Application Priority Data

Nov. 30, 2012 (EP) ..................................... 12195104

(51) Int. Cl.

| | |
|---|---|
| *A61K 31/4427* | (2006.01) |
| *C07D 401/06* | (2006.01) |
| *C07D 213/50* | (2006.01) |
| *A01N 43/40* | (2006.01) |
| *A01N 43/54* | (2006.01) |
| *A01N 43/56* | (2006.01) |
| *A01N 43/60* | (2006.01) |
| *A01N 43/76* | (2006.01) |
| *A01N 43/78* | (2006.01) |
| *C07D 401/14* | (2006.01) |
| *C07D 405/06* | (2006.01) |
| *C07D 413/06* | (2006.01) |

(Continued)

(52) U.S. Cl.
CPC .............. *C07D 213/50* (2013.01); *A01N 43/40* (2013.01); *A01N 43/54* (2013.01); *A01N 43/56* (2013.01); *A01N 43/60* (2013.01); *A01N 43/76* (2013.01); *A01N 43/78* (2013.01); *A01N 43/84* (2013.01); *C07D 213/46* (2013.01); *C07D 213/48* (2013.01); *C07D 213/52* (2013.01); *C07D 213/53* (2013.01); *C07D 213/61* (2013.01); *C07D 401/06* (2013.01); *C07D 401/14* (2013.01); *C07D 405/06* (2013.01); *C07D 413/06* (2013.01); *C07D 417/06* (2013.01)

(58) Field of Classification Search
CPC .......................... A61K 31/4427; C07D 401/06
USPC ........................................ 514/336; 546/268.1
See application file for complete search history.

(56) References Cited

U.S. PATENT DOCUMENTS

| | | | |
|---|---|---|---|
| 4,803,277 A | 2/1989 | Shiokawa et al. | |
| 4,876,263 A | 10/1989 | Shiokawa et al. | |

(Continued)

FOREIGN PATENT DOCUMENTS

| | | |
|---|---|---|
| CA | 2 808 144 | 3/2012 |
| CA | 2808144 | 3/2012 |

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Geffken et al., "Synthesis of 2-amino-imidazo[1,2-b][1,2,4]triazine-3,6,7(5H)-triones," Heterocyclic Communications, (2011), pp. 145-149.

(Continued)

*Primary Examiner* — Douglas M Willis
(74) *Attorney, Agent, or Firm* — Brinks Gilson & Lione

(57) ABSTRACT

The invention relates to pyridylidene compounds of formula (I), to the enantiomers, diastereomers and salts thereof and to compositions comprising such compounds. The invention also relates to methods and uses of these N-substituted pyridylidene compounds, and of compositions comprising thereof, for combating and controlling animal pests. Furthermore the invention relates also to pesticidal methods of applying such N-substituted pyridylidene compounds.

The N-substituted pyridylidene compounds of the present invention are defined by the following formula I:

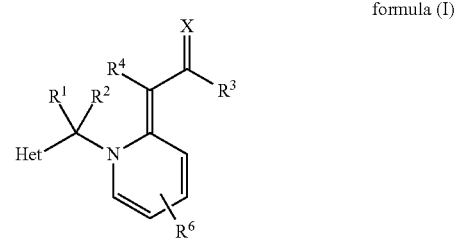

formula (I)

wherein X, Het, $R^1$, $R^2$, $R^3$, $R^4$ and $R^6$ are defined as in the description.

24 Claims, No Drawings

(51) Int. Cl.
   *C07D 417/06* (2006.01)
   *C07D 213/61* (2006.01)
   *C07D 213/46* (2006.01)
   *A01N 43/84* (2006.01)
   *C07D 213/48* (2006.01)
   *C07D 213/52* (2006.01)
   *C07D 213/53* (2006.01)

(56) References Cited

U.S. PATENT DOCUMENTS

| | | | |
|---|---|---|---|
| 5,719,306 | A | 2/1998 | Chandrakumar et al. |
| 6,838,462 | B2 | 1/2005 | Jeschke et al. |
| 7,951,951 | B2 | 5/2011 | Jeschke et al. |
| 8,106,211 | B2 | 1/2012 | Jeschke et al. |
| 8,106,212 | B2 | 1/2012 | Jeschke et al. |
| 8,563,584 | B2 | 10/2013 | Velten et al. |
| 2004/0209896 | A1 | 10/2004 | Jeschke et al. |
| 2009/0181947 | A1 | 7/2009 | Jeschke et al. |
| 2009/0247551 | A1 | 10/2009 | Jeschke et al. |
| 2011/0039894 | A1 | 2/2011 | Velten et al. |

FOREIGN PATENT DOCUMENTS

| | | |
|---|---|---|
| CH | 461489 | 8/1968 |
| DE | 19838138 | 3/1999 |
| DE | 102006015467 | 10/2007 |
| DE | 102006015470 | 10/2007 |
| EP | 0 259 738 | 3/1988 |
| EP | 0259738 | 3/1988 |
| EP | 0 268 915 | 6/1988 |
| EP | 0268915 | 6/1988 |
| EP | 0296453 | 12/1988 |
| EP | 0 639 569 | 2/1995 |
| EP | 0639569 | 2/1995 |
| WO | WO 9927929 | 6/1999 |
| WO | WO 02085915 | 10/2002 |
| WO | WO 2007115643 | 10/2007 |
| WO | WO 2007115647 | 10/2007 |
| WO | WO 2007125984 | 11/2007 |
| WO | WO 2009121507 | 10/2009 |
| WO | WO 2010005692 | 1/2010 |
| WO | WO 2012/029672 | 3/2012 |
| WO | WO 2012029672 | 3/2012 |
| WO | WO 2012136751 | 10/2012 |
| WO | WO 13/144213 | * 10/2013 |
| WO | WO 2013144088 | 10/2013 |
| WO | WO 2013144223 | 10/2013 |
| WO | WO 2013149903 | 10/2013 |

OTHER PUBLICATIONS

Jeschke et al., "Review Neonicotinoids—from Zero to Hero in Insecticide Chemistry," Pest Management Science, vol. 64, (2008), pp. 1084-1098.

Okazawa et al., "Three-Dimensional Quantitative Structure—Activity Relationship Analysis of Acyclic and Cyclic Chloronicotinyl Insecticides," Pest Management Science, vol. 56, (2000), pp. 509-515.

Reynolds et al., "The Structure of Certain Polyazaindenes. VII. 4-amino-6-methyl-1,3,3a,7-tetrazaindene and its Derivatives," J. Org. Chem., vol. 26, (1961), pp. 115-117.

International Search Report, PCT/EP2013/056540, filed Mar. 27, 2013, search completed May 24, 2013.

International Preliminary Report on Patentability, PCT/EP2013/056540, filed Mar. 27, 2013, report issued Oct. 1, 2014.

Carey, F.A., et al. "Advanced Organic Chemistry Part B: Reactions and Synthesis" 5th Edition, Springer Sciences + Business Media, LLC, 2007 New York, NY, p. 216-288.

Smith, M.B. et al. "March's Advanced Organic Chemistry", 6th Edition, John Wiley and Sons Inc., 2007, Hoboken, NJ, p. 960-964.

March "Advanced Organic Chemistry," second edition, pp. 104-105 and 113 (1977).

* cited by examiner

N-SUBSTITUTED PYRIDINYLIDENES FOR COMBATING ANIMAL PESTS

CROSS-REFERENCE TO RELATED APPLICATIONS

This application is a National Stage application of International Application No. PCT/EP2013/056540, filed Mar. 27, 2013, which claims the benefit of U.S. Provisional Application No. 61/617,706, filed Mar. 30, 2012, and U.S. Provisional Application No. 61/731,515, filed Nov. 30, 2012. This application also claims priority under 35 U.S.C. §119 to EP Patent Application No. 12195104.0, filed Nov. 30, 2012.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates to N-substituted pyridinylidene compounds, to the enantiomers, diastereomers, derivatives and salts thereof and to compositions comprising such compounds. The invention also relates to the use of the N-substituted pyridinylidene compounds, of their salts or of compositions comprising them for combating animal pests. Furthermore the invention relates also to methods of applying such compounds.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

It is therefore an object of the present invention to provide compounds having a good pesticidal activity, especially against difficult to control insects and acaridae.

It has been found that these objects are solved by N-substituted pyridinylidene derivatives of the general formula I:

N-substituted pyridinylidene compounds of the general formula (I):

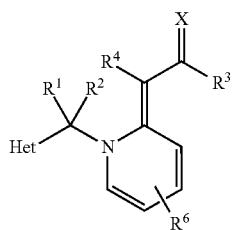

wherein
X is selected from O, S, or $NR^5$;
Het is a 5 or 6 membered carbon-bound or optionally nitrogen-bound heterocyclic or heteroaromatic ring system, each ring members selected from carbon atoms and at least one, up to three heteroatoms independently selected from sulfur, oxygen or nitrogen, wherein the carbon, oxygen and nitrogen ring members can independently be partly or fully oxidized, and wherein each ring of the ring system is optionally substituted by k substituents selected from $R^{6a}$, wherein k is an integer selected from 1, 2, 3, 4, or 5, and two or more substituents $R^{6a}$ are selected independently from one another;
$R^1$, $R^2$ are independently from each other selected from the group consisting of hydrogen, halogen, cyano, nitro, —SCN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-alkylthio, wherein each of the aforementioned carbon chain radicals are unsubstituted, partly or completely halogenated or may carry any combination of one or more radicals $R^7$, $Si(R^{11})_2R^{12}$, $OR^{16}$, $OSO_2R^{16}$, $S(O)_nR^{16}$, $S(O)_nNR^{17a}R^{17b}$, $NR^{17a}R^{17b}$, $C(=O)NR^{17a}R^{17b}$, $C(=S)NR^{17a}R^{17b}$, $C(=O)OR^{16}$, $C(=O)R^{15}$, $C(=S)R^{15}$, phenyl, optionally substituted with one or more, e.g. 1, 2, 3, 4 or 5 substituents $R^{18}$, which are independently selected from one another,
a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4, substituents $R^{18}$, selected independently from one another, and wherein the nitrogen and/or the sulfur atom(s) of the heterocyclic ring may optionally be oxidized,
or
$R^1$ and $R^2$ from, together with the carbon atom, which they attached to, a 3- to 6-membered saturated or partly unsaturated carbocyclic or heterocyclic ring, wherein each of the carbon atoms of said cycle are unsubstituted or may carry any combination of 1 or 2 radicals $R^7$,
or
$R^1$ and $R^2$ may together be =O, =$CR^{13}R^{14}$; =S; =$S(O)_nR^{16}$; =$S(O)_nNR^{17a}R^{17b}$, =$NR^{17a}$, =$NOR^{16}$; =$NNR^{17a}$;
$R^3$ is selected from hydrogen, halogen, cyano, SCN, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkinyl, wherein each of the eight last mentioned carbon chain radicals are unsubstituted, partly or completely halogenated or may carry any combination of one or more radicals $R^7$;
$OR^8$, $OSO_2R^8$, $S(O)_nR^8$, $S(O)_nNR^{9a}R^{9b}$, $NR^{9a}R^{9b}$, $C(=O)NR^{9a}R^{9b}$, $C(=S)NR^{9a}R^{9b}$, $C(=O)R^7$, $C(=S)R^7$,
phenyl, optionally substituted with one or more, e.g. 1, 2, 3, 4 or 5 substituents $R^{10}$, which are independently selected from one another,
a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4 substituents $R^{18}$, selected independently from one another, and wherein the nitrogen and/or the sulfur atom(s) of the heterocyclic ring may optionally be oxidized;

$R^4$ is selected from the group consisting of hydrogen, halogen, cyano, nitro, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-alkylthio, wherein each of the six last mentioned carbon chain radicals are unsubstituted, partly or completely halogenated or may carry any combination of one or more radicals $R^7$, Si($R^{11}$)$_2R^{12}$, O$R^{16}$, OSO$_2R^{16}$, S(O)$_nR^{16}$, S(O)$_n$N$R^{17a}R^{17b}$, N$R^{17a}R^{17b}$, C(=O)N$R^{17a}R^{17b}$, C(=S)N$R^{17a}R^{17b}$, C(=O)O$R^{16}$, C(=O)$R^{15}$, C(=S)$R^{15}$, phenyl, optionally substituted with 1, 2, 3, 4 or 5 substituents $R^{18}$, which are independently selected from one another, a 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with one or more, e.g. 1, 2, 3 or 4, substituents $R^{10}$, selected independently from one another, and wherein the nitrogen and/or the sulfur atom(s) of the heterocyclic ring may optionally be oxidized;

$R^5$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $R^7$, phenyl, benzyl, pyridyl, pyrimidyl, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy or ($C_1$-$C_6$-alkoxy)carbonyl, $R^6$, $R^{6a}$ are each, independently from the number of $R^6$ or $R^{6a}$ present and independently from one another, selected from the group consisting of hydrogen, halogen, cyano, azido, nitro, SCN, SF$_5$, $C_1$-$C_{10}$-alkyl, $C_3$-$C_8$-cycloalkyl, $C_2$-$C_{10}$-alkenyl, $C_2$-$C_{10}$-alkinyl, and wherein the carbon atoms of the aforementioned aliphatic and cyclo-aliphatic radicals may optionally be further substituted independently from one another with one or more $R^7$, O$R^8$, N$R^{9a}R^{9b}$, S(O)$_nR^8$, S(O)$_n$N$R^{9a}R^{9b}$, C(=O)$R^7$, C(=O)N$R^{9a}R^{9b}$, C(=O)O$R^8$, C(=S)$R^7$, C(=S)N$R^{9a}R^{9b}$, C(=S)O$R^8$, C(=S)S$R^8$, C(=N$R^{9a}$)$R^7$, C(=N$R^{9a}$)N$R^{9a}R^{9b}$, Si($R^{11}$)$_2R^{12}$;

phenyl, optionally substituted with 1, 2, 3, 4 or 5 substituents selected independently from $R^{10}$;

a 3-, 4-, 5-, 6- or 7-membered saturated, partly saturated or unsaturated aromatic heterocyclic ring comprising 1, 2, 3 or 4 heteroatoms selected from oxygen, nitrogen and/or sulfur, optionally substituted with 1, 2, 3, 4 or 5 substituents selected independently from $R^{10}$, and wherein the nitrogen and/or the sulfur atom(s) of the heterocyclic ring may optionally be oxidized;

or two of $R^6$ or two of $R^{6a}$ present on one ring carbon or sulfur atom may together form =O, =C$R^{13}R^{14}$; =S; =S(O)$_nR^{16}$; =S(O)$_n$N$R^{17a}R^{17b}$, =N$R^{17a}$, =NO$R^{16}$; =NN$R^{17a}$;

or two $R^6$ together form a $C_2$-$C_7$ alkylene chain, thus forming, together with the ring atom(s) to which they are bound, a 3-, 4-, 5-, 6-, 7- or 8-membered ring, where the alkylene chain may be interrupted by 1 or 2 O, S and/or N$R^{17a}$ and/or 1 or 2 of the CH$_2$ groups of the alkylene chain may be replaced by a group C=O, C=S and/or C=N$R^{17a}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by one or more, e.g. 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{18}$;

$R^7$ is each independently from one another selected from the group consisting of hydrogen, halogen, cyano, azido, nitro, —SCN, SF$_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, Si($R^{11}$)$_2R^{12}$; O$R^{16}$, OSO$_2R^{16}$, S(O)$_nR^{16}$, S(O)$_n$N$R^{17a}R^{17b}$, N$R^{17a}R^{17b}$, C(=O)N$R^{17a}R^{17b}$, C(=S)N$R^{17a}R^{17b}$; C(=O)O$R^{16}$, C(=O)$R^{15}$, C(=S)$R^{15}$, C(=N$R^{17a}$)$R^{15}$, phenyl, optionally substituted with 1, 2, 3, 4 or 5 substituents $R^{10}$, which are independently selected from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4 substituents $R^{10}$, selected independently from one another, and wherein the nitrogen and/or the sulfur atom(s) of the heterocyclic ring may optionally be oxidized, or two $R^7$ present on one carbon atom may together form =O, =C$R^{13}R^{14}$; =S; =S(O)$_nR^{16}$; =S(O)$_n$N$R^{17a}R^{17b}$, =N$R^{17a}$, =NO$R^{16}$; =NN$R^{17a}$;

or two $R^7$ may form a 3-, 4-, 5-, 6-, 7- or 8-membered saturated or partly unsaturated carbocyclic or heterocyclic ring together with the carbon atoms to which the two $R^7$ are bonded to;

$R^8$ is each independently from one another selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, —Si($R^{11}$)$_2R^{12}$, S(O)$_nR^{16}$, S(O)$_n$N$R^{17a}R^{17b}$, N$R^{17a}R^{17b}$, —N=C$R^{13}R^{14}$, —C(=O)$R^{15}$, C(=O)N$R^{17a}R^{17b}$, C(=S)N$R^{17a}R^{17b}$, C(=O)O$R^{16}$, phenyl, optionally substituted with one or more substituents $R^{10}$; which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4 substituents $R^{10}$, selected independently from one another, and wherein the nitrogen and/or the sulfur atom(s) of the heterocyclic ring may optionally be oxidized;

$R^{9a}$, $R^{9b}$ are each independently from one another selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $S(O)_n R^{16}$, —$S(O)_n NR^{17a}R^{17b}$, $C(=O)R^{15}$, $C(=O)R^{16}$, $C(=O)NR^{17a}R^{17b}$, $C(=S)R^{15}$, $C(=S)SR^{16}$, $C(=S)NR^{17a}R^{17b}$, $C(=NR^{17a})R^{18}$;

phenyl, optionally substituted with one or more, e.g. 1, 2, 3 or 4, substituents $R^{10}$, which are selected independently from one another;

a 3-, 4-, 5-, 6- or 7-membered saturated, partly saturated or unsaturated aromatic heterocyclic ring comprising 1, 2, 3 or 4 heteroatoms selected from oxygen, nitrogen and/or sulfur, optionally substituted with 1, 2, 3 or 4 substituents $R^{10}$, selected independently from one another, and wherein the nitrogen and/or the sulfur atom(s) of the heterocyclic ring may optionally be oxidized;

or, $R^{9a}$ and $R^{9b}$ are together a $C_2$-$C_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteroatoms selected from oxygen, sulfur or nitrogen, and may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_6$-cycloalkyl, $C_3$-$C_6$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally substituted with one or more substituents $R^{10}$; which are selected independently from one another, a 3-, 4-, 5-, 6-, or 7-membered saturated, partly saturated or unsaturated aromatic heterocyclic ring comprising 1, 2 or 3 heteroatoms selected from oxygen, nitrogen and/or sulfur, optionally substituted with one or more substituents $R^{10}$, selected independently from one another, and wherein the nitrogen and/or the sulfur atom(s) of the heterocyclic ring may optionally be oxidized;

or $R^{9a}$ and $R^{9b}$ together may form a =$CR^{13}R^{14}$, =$S(O)_n R^{16}$, =$S(O)_n NR^{17}R^{17}$, =$NR^{17}$ or =$NOR^{16}$ radical;

$R^{10}$ is each independently from one another selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^{15}$, which are selected independently from one another, $Si(R^{11})_2R^{12}$, $OR^{16}$, $OS(O)_n R^{16}$, —$S(O)_n R^{16}$, $S(O)_n NR^{17a}R^{17b}$, $NR^{17a}R^{17b}$, $C(=O)R^{15}$, $C(=S)R^{15}$, $C(=O)OR^{16}$, —$C(=NR^{17a})R^{15}$, $C(=O)NR^{17a}R^{17b}$, $C(=S)NR^{17a}R^{17b}$, phenyl, optionally substituted with halogen, cyano, nitro, $C_1$-$C_6$-alkyl, $C_1$-$C_6$-haloalkyl, $C_1$-$C_6$-alkoxy or $C_1$-$C_6$-haloalkoxy, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with one or more substituents selected independently from one another from halogen, cyano, $NO_2$, $C_1$-$C_6$-alkyl, $C_1$-$C_6$-haloalkyl, $C_1$-$C_6$-alkoxy or $C_1$-$C_6$-haloalkoxy, and wherein the nitrogen and/or the sulfur atom(s) of the heterocyclic ring may optionally be oxidized;

or two $R^{10}$ present together on one atom of a partly saturated heterocyclic may be =O, =$CR^{13}R^{14}$; =$S(O)_n R^{16}$; =$S(O)_n NR^{17a}R^{17b}$, =$NR^{17a}$, =$NOR^{16}$ or =$NNR^{17a}$;

or, two $R^{10}$ on adjacent carbon atoms may be a bridge selected from $CH_2CH_2CH_2CH_2$, CH=CH—CH=CH, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^{17a}$, $CH_2CH$=N, CH=CH—$NR^{17a}$, OCH=N, SCH=N and form together with the carbon atoms to which the two $R^{10}$ are bonded to a 5-membered or 6-membered partly saturated or unsaturated, aromatic carbocyclic or heterocyclic ring, wherein the ring may optionally be substituted with one or two substituents selected from =O, OH, $CH_3$, $OCH_3$, halogen, cyano, halomethyl or halomethoxy;

$R^{11}$, $R^{12}$ (are each independently from one another selected from the group consisting of hydrogen, halogen, $C_1$-$C_6$ alkyl, $C_1$-$C_6$ haloalkyl, $C_1$-$C_6$ alkoxy, $C_1$-$C_6$ alkoxyalkyl, $C_2$-$C_6$ alkenyl, $C_2$-$C_6$ haloalkenyl, $C_2$-$C_6$ alkinyl, $C_2$-$C_6$ haloalkinyl, $C_3$-$C_8$ cycloalkyl, $C_3$-$C_5$ halocycloalkyl, $C_1$-$C_6$ alkoxyalkyl, $C_1$-$C_6$ haloalkoxyalkyl and phenyl, optionally substituted with one or more substituents $R^{18}$; which are selected independently from one another;

$R^{13}$, $R^{14}$ are each independently from one another selected from the group consisting of hydrogen, $C_1$-$C_4$ alkyl, $C_1$-$C_6$ cycloalkyl, $C_1$-$C_4$ alkoxyalkyl, phenyl and benzyl;

$R^{15}$ is each independently from one another selected from the group consisting of hydrogen, halogen, cyano, nitro, OH, SH, SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tenbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxgenated and/or may carry 1 or 2 radicals selected from $C_1$-$C_4$ alkoxy;

phenyl, benzyl, pyridyl, phenoxy, wherein the last four radicals may be unsubstituted, partially or fully halogenated and/or to carry 1, 2 or 3 substituents selected from $C_1$-$C_6$-alkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino, or two $R^{15}$ present on the same carbon atom may together be =O, =CH($C_1$-$C_4$), =C($C_1$-$C_4$-alkyl)$C_1$-$C_4$-alkyl, =N($C_1$-$C_6$-alkyl) or =NO($C_1$-$C_6$-alkyl);

$R^{16}$ is each independently from one another selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_3$-$C_8$-cycloalkyl, wherein the four last mentioned radicals may be unsubstituted, partially or fully halogenated and/or oxygenated and/or may carry 1 or 2 radicals selected from $C_1$-$C_4$ alkoxy, phenyl, benzyl, pyridyl, phenoxy, wherein the last four radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy or ($C_1$-$C_6$-alkoxy)carbonyl;

$R^{17a}$, $R^{17b}$ are each independently from one another selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfonyl, $C_1$-$C_6$-haloalkylthio, trimethylsilyl, triethylsilyl, tenbutyldimethylsilyl, $C_1$-$C_6$-alkyl, $C_2$-$C_6$-alkenyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy or ($C_1$-$C_6$-alkoxy)carbonyl, or, $R^{17a}$ and $R^{17b}$ may together be a $C_2$-$C_5$ alkylene chain forming a 3- to 7-membered saturated, partly saturated or unsaturated ring together with the nitrogen atom $R^{17a}$ and $R^{17b}$ are bonded to, wherein the alkylene chain may contain 1 or 2 heteroatoms selected from oxygen, sulfur or nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

n is an integer selected independently from one another from 0, 1 or 2;

and/or an enantiomer, diastereomer, E/Z-isomer or agriculturally or veterinarily acceptable salts thereof for controlling and/or combating animal pests.

2. Description of Related Art

Certain heteroarylalkyl-substituted 5- and 6-membered heterocycles and their use as insecticide have been described in DE 3639877.

Nitromethyl)pyridinium compounds and their insecticidal activity are disclosed in DE 2416350. The preparation of (N-heterocyclylimino)heterocyclic compounds as insecticides is disclosed in WO 9215564.

Benzoyl substituted like the compound S24795 have been disclosed as alpha-7 Nicotinic Receptor Interactors in Journal of Neuroscience 2009), 29(35), 10961-10973.

Substituted pyridinylidene carbonyl compounds and their chemistry are described in *Journal of the Chemical Society* [Section] 1967, 167(10), 983-988, *Journal of the Chemical Society* 1965, 3093-3096, *Australian Journal of Chemistry* 1972, 5(7), 1549-1560 and *Khimiya Geterotsiklich-eskikh Soedinenii* 1991 (8), 1110-1116. Pyridine-imine compounds and methods for producing them are described in WO2012/029672 and WO/2013/031671.

BRIEF SUMMARY OF THE INVENTION

The N-substituted pyridinylidene compounds of the formula I, and their agriculturally or veterinarily acceptable salts are highly active against animal pest, i.e. harmful arthropodes and nematodes, especially against difficult to control insects and acaridae.

BRIEF DESCRIPTION OF THE SEVERAL VIEWS OF THE DRAWING(S)

Not applicable.

DETAILED DESCRIPTION OF THE INVENTION

Accordingly, the present invention relates to N-substituted pyridinylidene compounds of the general formula I, to their agriculturally or veterinarily useful salts, their enantiomers or diasteromers.

Moreover, the present invention relates to and includes the following embodiments:

agricultural and veterinary compositions comprising an amount of at least one compound of the formula I or an enantiomer, diasteromer or salt thereof;

the use of a compound of formula I or an enantiomer, diasteromer or salt thereof for combating animal pests;

a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of the formula I or an enantiomer, diasteromer or salt thereof;

a method for protecting crops from attack or infestation by animal pests, which comprises contacting a crop with a pesticidally effective amount of at least one compound of the formula I or an enantiomer, diasteromer or salt thereof;

a method for the protection of plant propagation, especially seeds, from soil insects and of the seedlings' roots and shoots from soil and foliar insects comprising contacting the seeds before sowing and/or after pregermination with at least one compound of the formula I, or the enantiomers, diastereomers or salts thereof;

seeds comprising a compound of the formula I or an enantiomer, diasteromer or salt thereof;

the use of compounds of formula I or the enantiomers, diastereomers or veterinary acceptable salts thereof for combating parasites in and on animals.

a method for treating, controlling, preventing or protecting animals against infestation or infection by parasites which comprises orally, topically or parenterally administering or applying to the animals a parasiticidally effective amount of an compound of formula I or the enantiomers, diastereomers and/or veterinary acceptable salt thereof;

a process for the preparation of a veterinary composition for treating, controlling, preventing or protecting animals against infestation or infection by parasites which comprises adding a parasiticidally effective amount of an compound of formula I or the enantiomers, diastereomers and/or veterinary acceptable salt thereof to a carrier composition suitable for veterinary use;

the use of a compound of formula I or the enantiomers, diastereomers and/or veterinary acceptable salt thereof for the preparation of a medicament for treating, controlling, preventing or protecting animals against infestation or infection by parasites;

The present invention especially relates to plant propagation materials, in particular as mentioned above to seeds, comprising at least one compound of formula I and/or an agriculturally acceptable salt thereof.

The present invention relates to every possible stereoisomer of the compounds of formula I, i.e. to single enantiomers or diastereomers, as well as to mixtures thereof.

The present invention relates also to the respective E and Z isomers of compounds of gerenral formula (I):

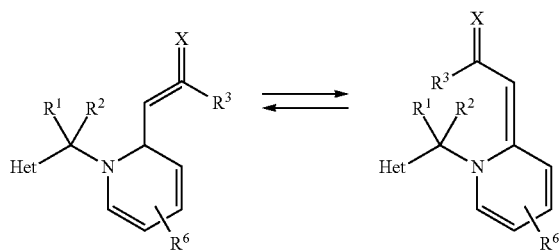

The present invention relates to each isomer alone, or mixtures or combinations of the isomers in any proportion to each other.

The compounds of the present invention may be amorphous or may exist in one ore more different crystalline states (polymorphs) or modifications which may have a different macroscopic properties such as stability or show different biological properties such as activities. The present invention includes both amorphous and crystalline compounds of the formula I, mixtures of different crystalline states or modifications of the respective compound I, as well as amorphous or crystalline salts thereof.

Salts of the compounds of the formula I are preferably agriculturally and/or veterinary acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, futher $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, ch lorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as ch loromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring containing 1, 2 or 3 heteroatoms" or "containing heteroatom groups", wherein those heteroatom(s) (group(s)) are selected from N, O, S, NO, SO and $SO_2$ and are ring members, as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: Oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 3,4 dihydrooxazol-3-yl, 3,4-dihydrooxazol-4-yl, 3,4-dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclyl (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4 thiazolyl, 5-thiazo-dyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

Embodiments and preferred compounds of the present invention are outlined in the following paragraphs.

The remarks made below concerning preferred embodiments of the variables of the compounds of formula I, especially with respect to their substituents X, Het, $R^1$, $R^2$, $R^3$, $R^4$ and $R^6$ are valid both on their own and, in particular, in every possible combination with each other.

When # appears in a formula showing a preferred substructure of a compound of the present invention, it denotes the attachment bond in the remainder molecule.

Preferred are compounds of formula (I), wherein Het is selected from the group consisting of radicals of formulae Het-1 to Het-24:

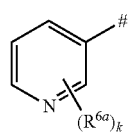
Het-1

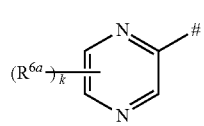
Het-2

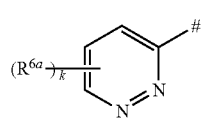
Het-3

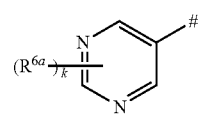
Het-4

-continued

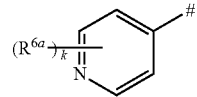
Het-5

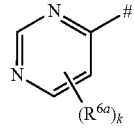
Het-6

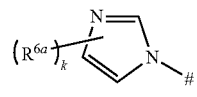
Het-7

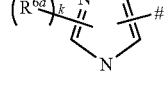
Het-8

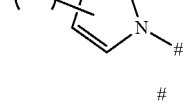
Het-9

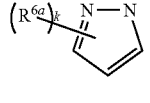
Het-10

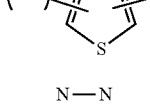
Het-11

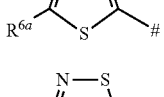
Het-12

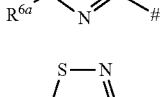
Het-13

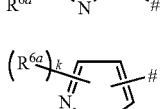
Het-14

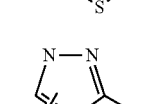
Het-15

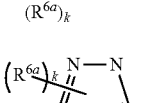
Het-16

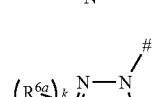
Het-17

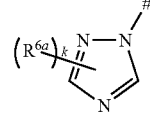
Het-18

-continued

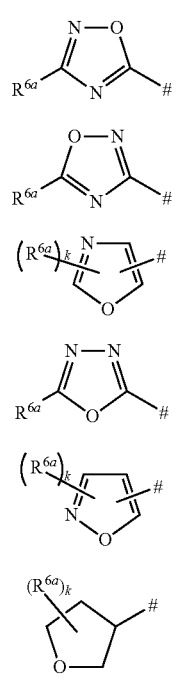

Het-19

Het-20

Het-21

Het-22

Het-23

Het-24 wherein # denotes the bond in formula (I), k is 0, 1 or 2 and Rha has the preferred meaning as defined further below.

Especially preferred are compounds of formula (I), wherein Het is selected from the group consisting of radicals of formulae Het-1, Het-11a and Het-24:

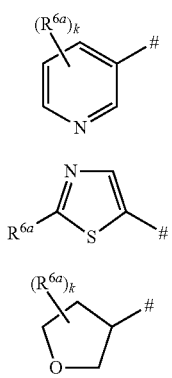

Het-1

Het-11a

Het-24 and wherein # denotes the bond in formula (I), k is 0, 1 or 2 and $R^{6a}$ has the preferred meaning as defined further below.

Especially more preferred are compounds of formula (I), wherein Het is Het-1a:

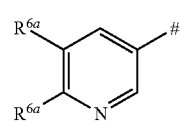

Het-1 and wherein # denotes the bond in formula (I), and $R^{6a}$ has the preferred meaning as defined further below.

Especially more preferred are compounds of formula (I), wherein Het is Het-11a:

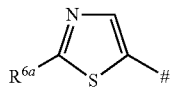

Het-11a and wherein # denotes the bond in formula (I), and $R^{6a}$ has the preferred meaning as defined further below.

Preferred are compounds of formula (I), wherein k is 0, 1 or 2.

Especially preferred are compounds of formula (I), wherein k is 0, 1 or 2 and $R^{6a}$ has the preferred meaning as defined herein below.

Preferred are compounds of formula (I), wherein Het is substituted with $R^{6a}$ selected each independently from one another from the group consisting of hydrogen, halogen, cyano, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be further substituted independently from one another with one or more $R^7$, $OR^8$, $NR^{9a}R^{9b}$, $S(O)_nR^8$, $S(O)_nNR^{9a}R^{9b}$, $C(=O)R^7$, $C(=O)NR^{9a}R^{9b}$, $C(=O)OR^8$, $C(=S)R^7$, $C(=S)NR^{9a}R^{9b}$, $C(=NR^{9a})R^7$, $C(=NR^{9a})NR^{9a}R^{9b}$.

Especially preferred are compounds of formula (I), wherein Het is substituted with $R^{6a}$ selected each independently from one another from the group consisting of hydrogen, halogen, $C_1$-$C_4$-alkoxy or $C_1$-$C_4$-alkyl, wherein the carbon atoms of the latter two radicals may be partially of fully halogenated.

Preferred are compounds of formula (I), wherein X is selected from O.

Preferred are compounds of formula (I), wherein X is selected from S.

Preferred are compounds of formula (I), wherein X is selected from $NR^5$, and $R^5$ is selected from is selected from the group consisting of hydrogen, cyano, $C_1$-$C_6$-alkyl, $C_1$-$C_6$-alkoxy, $C_1$-$C_6$-alkylthio, $C_3$-$C_8$-cycloalkyl, wherein each of the four last mentioned radicals are unsubstituted, partly or completely halogenated or may carry any combination of one or more radicals $R^7$;

Preferred are compounds of formula (I), wherein $R^1$ and $R^2$ are independently from each other selected from the group consisting of hydrogen, halogen, CN, $C_1$-$C_6$-alkyl, $C_3$-$C_6$-cycloalkyl, $C_1$-$C_6$-haloalkyl, $C_2$-$C_6$-halocycloalkyl; or
$R^1$ and $R^2$ may together be =O, =$CR^{13}R^{14}$ or =S, or
$R^1$ and $R^2$ form, together with the carbon atom, which they attached to, a 3- to 5 membered saturated carbocyclic ring;

Especially preferred are compounds of formula (I), wherein $R^1$ and $R^2$ are independently from each other selected from the group consisting of hydrogen, halogen, cyano, $C_1$-$C_3$-alkyl or $C_1$-$C_3$-haloalkyl Especially more preferred are compounds of formula (I), wherein $R^1$ and $R^2$ are both hydrogen.

Preferred are compounds of formula (I), wherein $R^3$ is selected from hydrogen, halogen, cyano, SCN, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkinyl, wherein each of the eight last mentioned radicals are unsubstituted, partly or completely halogenated or may carry any combination of one or more radicals $R^7$,
$OR^8$, $S(O)_nR^8$, $NR^{9a}R^{9b}$,
phenyl, optionally substituted with 1, 2, 3, 4 or 5 substituents $R^{10}$, which are independently selected from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4, substituents $R^{18}$, selected independently from one another, and wherein the nitrogen and/or the sulfur atom(s) of the heterocyclic ring may optionally be oxidized.

Especially preferred are compounds of formula (I), wherein $R^3$ is selected from hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $OR^{15}$, $S(O)_nR^{16}$, $NR^{17a}R^{17b}$, phenyl, optionally substituted with one or more, e.g. 1, 2 or 3 substituents $R^{10}$, which are independently selected from one another, or a 5- or 6-membered heteroaromatic ring comprising 1, 2 or 3 heteroatoms selected from oxygen, nitrogen and/or sulfur, optionally substituted with one or more, e.g. 1, 2, or 3 substituents $R^{10}$, selected independently from one another, and wherein the nitrogen and/or the sulfur atom(s) of the heterocyclic ring may optionally be oxidized Especially preferred are compounds of formula (I), wherein $R^4$ is selected from the group consisting of hydrogen, halogen, cyano, nitro, $C_1$-$C_4$-alkyl, $C_3$-$C_6$-cycloalkyl, $C_1$-$C_4$-alkoxy, $C_1$-$C_4$-alkylthio, wherein each of the four last mentioned radicals are unsubstituted, partly or completely halogenated or may carry any combination of one or more radicals $R^7$.

Preferred are compounds of formula (I), wherein each $R^6$ is selected from the group consisting of hydrogen, halogen, cyano, $C_1$-$C_{10}$-alkyl, $C_3$-$C_8$-cycloalkyl, $C_2$-$C_{10}$-alkenyl, $C_2$-$C_{10}$-alkinyl, and wherein the carbon atoms of the aforementioned aliphatic and cyclo-aliphatic radicals may optionally be further substituted independently from one another with one or more $R^7$, $OR^8$, $NR^{9a}R^{9b}$, $S(O)_nR^8$, $S(O)_n$ $NR^{9a}R^{9b}$, $C(=O)R^7$, $C(=O)NR^{9a}R^{9b}$, $C(=O)OR^8$, $C(=S)R^7$, $C(=S)NR^{9a}R^{9b}$, $C(=NR^{9a})R^7$, $C(=NR^{9a})NR^{9a}R^{9b}$.

Especially preferred are compounds of formula (I), wherein $R^6$ is selected from hydrogen, halogen, cyano, $C_1$-$C_4$-alkoxy or $C_1$-$C_4$-alkyl, wherein the carbon atoms of the latter two radicals may be partially of fully halogenated, or $OR^{16}$, $NR^{17a}R^{17b}$, $S(O)_nR^{16}$;

Especially more preferred are compounds of formula (I), wherein Het is selected from the group consisting of radicals of formulae Het-1, Het-11a and Het-24:

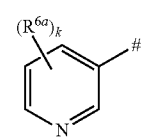

Het-1

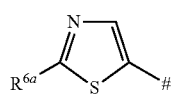

Het-11a

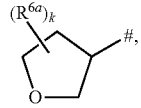

Het-24 wherein # denotes the bond in formula (I), and wherein $R^{6a}$ is selected from hydrogen, halogen, $C_1$-$C_4$-alkoxy or $C_1$-$C_4$-alkyl, wherein the carbon atoms of the latter two radicals may be partially of fully halogenated; k is 0, 1 or 2; X is selected from O or S; $R^1$, $R^2$ are independently from each other selected from the group consisting of hydrogen, halogen, cyano, $C_1$-$C_3$-alkyl, or $C_1$-$C_3$-haloalkyl; $R^4$ is selected from the group consisting of hydrogen, halogen, cyano, nitro, $C_1$-$C_4$-alkyl, $C_3$-$C_6$-cycloalkyl, $C_1$-$C_4$-alkoxy, $C_1$-$C_4$-alkylthio, wherein each of the four last mentioned radicals are unsubstituted, partly or completely halogenated; and $R^6$ is selected from hydrogen, halogen, cyano, $C_1$-$C_4$-alkoxy or $C_1$-$C_4$-alkyl, wherein the carbon atoms of the latter two radicals may be partially of fully halogenated.

Especially more preferred are compounds of formula (I), wherein Het is Het-1 or Het-11a:

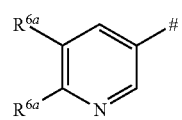

Het-1

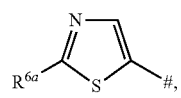

Het-11a wherein # denotes the bond in formula (I), and wherein $R^{6a}$ is selected from hydrogen, halogen or $C_1$-$C_4$-haloalkyl; X is selected from O or S; $R^1$, $R^2$ are both hydrogen; $R^3$ is selected from hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $OR^{15}$, $S(O)_n$ $R^{16}$, $NR^{17a}R^{17b}$, phenyl, optionally substituted with one or more, e.g. 1, 2 or 3 substituents $R^{10}$, which are independently selected from one another, or a 5- or 6-membered heteroaromatic ring comprising 1, 2 or 3 heteroatoms selected from oxygen, nitrogen and/or sulfur, optionally substituted with one or more, e.g. 1, 2, or 3 substituents $R^{10}$, selected independently from one another, and wherein the nitrogen and/or the sulfur atom(s) of the heterocyclic ring may optionally be oxidized;

$R^4$ is selected from the group consisting of hydrogen, halogen, cyano, $C_3$-$C_6$-cycloalkyl, $C_1$-$C_4$-alkoxy, $C_1$-$C_4$-alkylthio, wherein each of the four last mentioned radicals are unsubstituted, partly or completely halogenated; and $R^6$ is selected from hydrogen, halogen, cyano, $C_1$-$C_4$-alkoxy or $C_1$-$C_4$-alkyl, wherein the carbon atoms of the latter two radicals may be partially of fully halogenated.

Preferred examples are compounds of the present invention are compounds of the following formulae I-1 to I-128.

Especially preferred examples are compounds of the following formulae I-1 to I-128, wherein the variable $R^3$ has one of the preferred meanings given in the table C below:

-continued

I-14 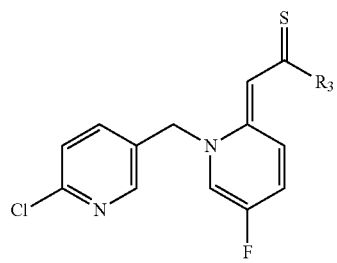
I-15 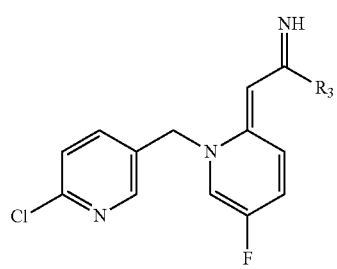
I-16 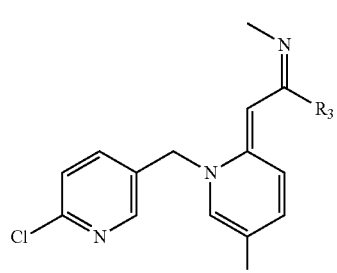
I-17 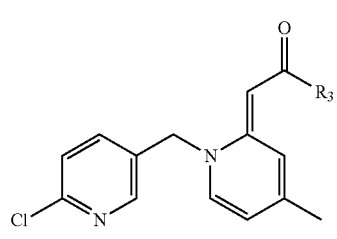
I-18 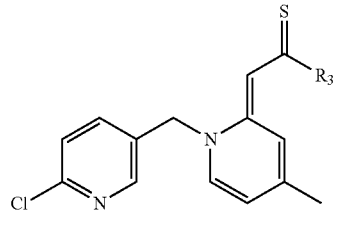
I-19 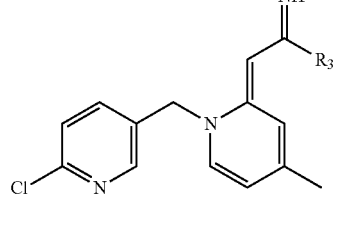
I-20 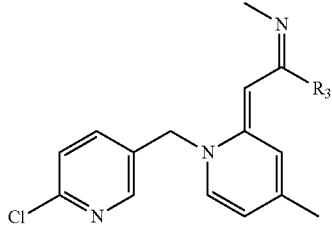
I-21 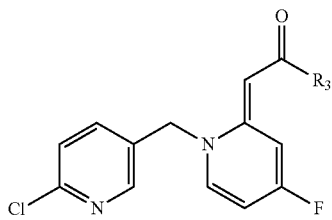
I-22 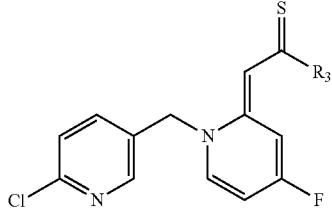
I-23 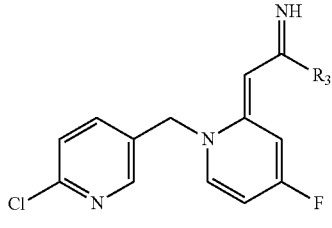
I-24 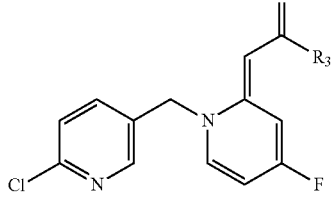
I-25 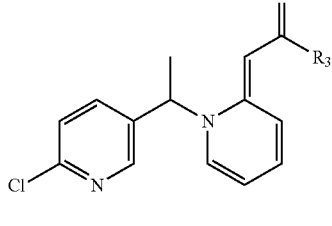
I-26 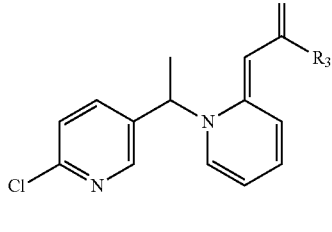

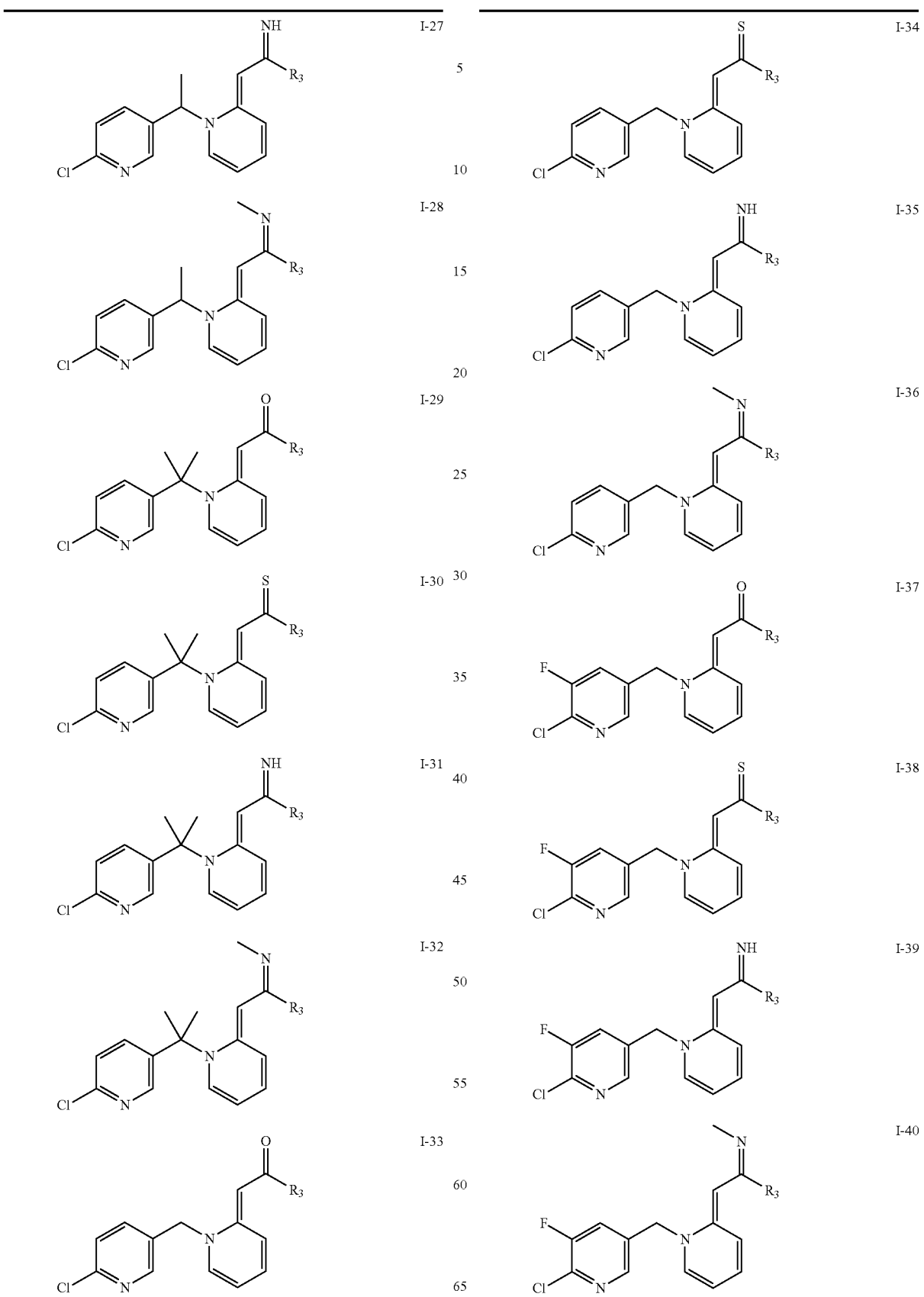

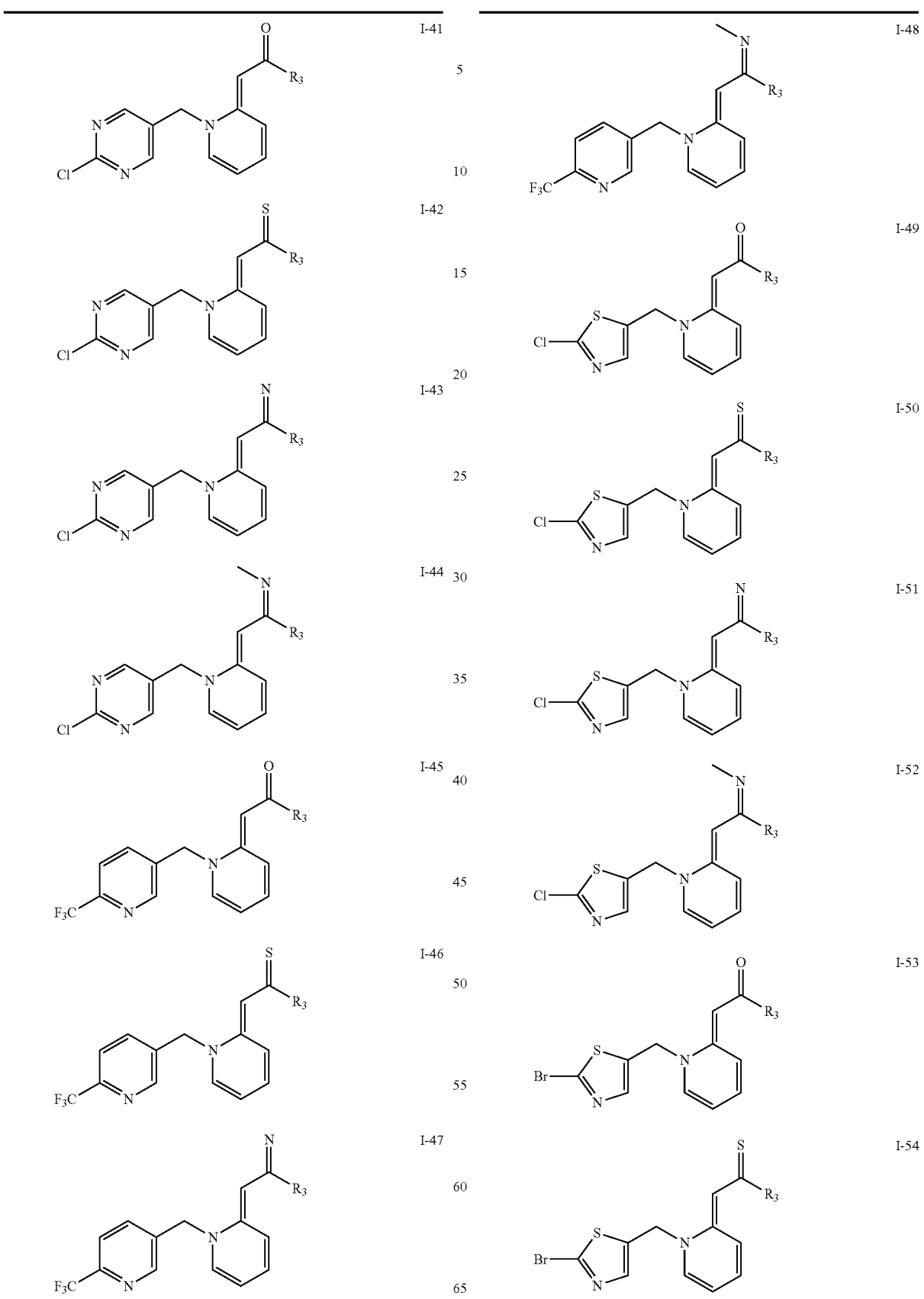

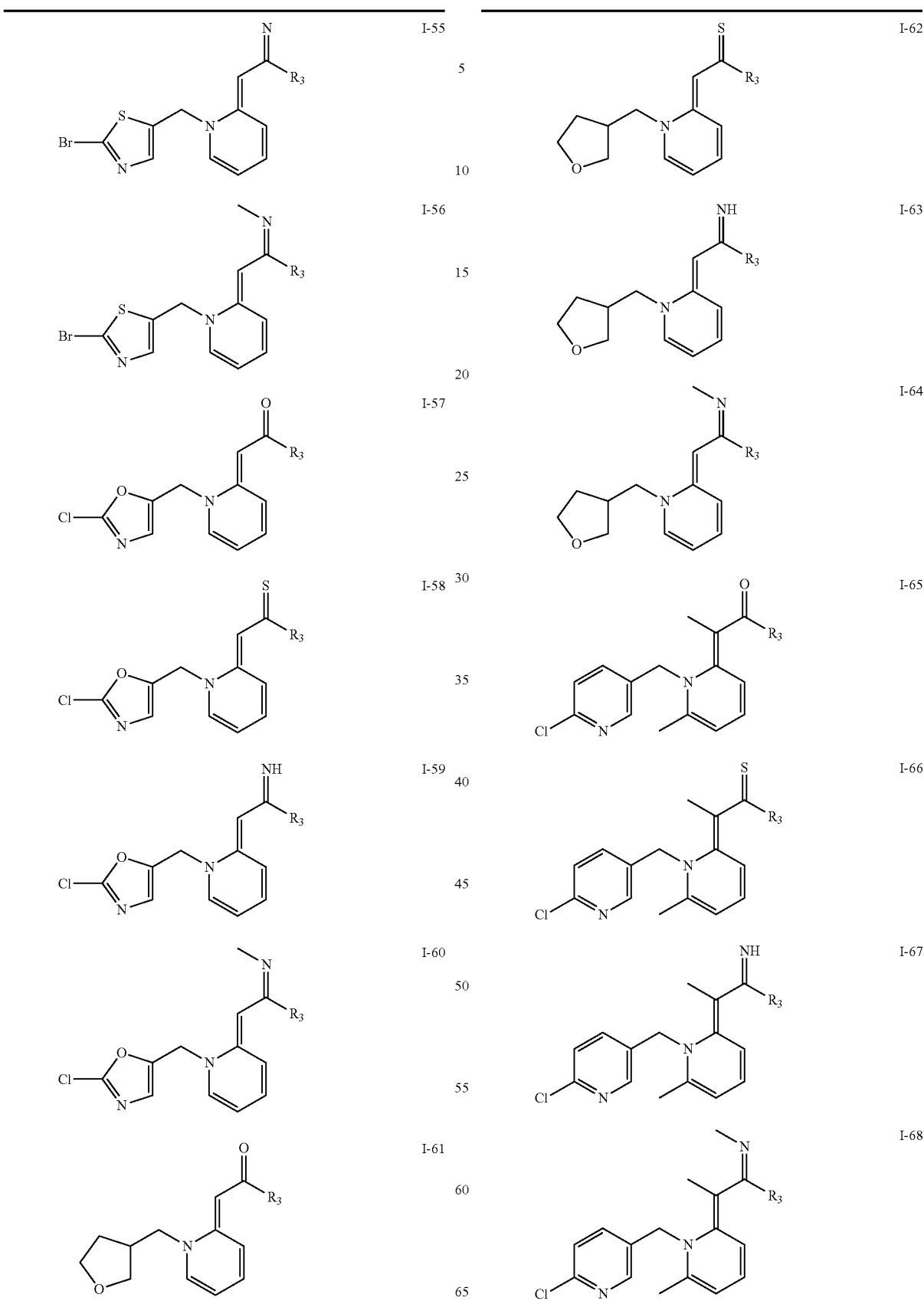

| | |
|---|---|
| 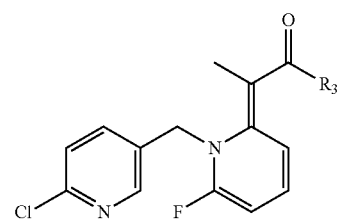 I-69 | 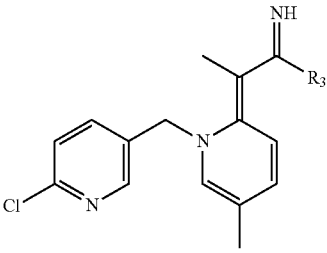 I-75 |
| 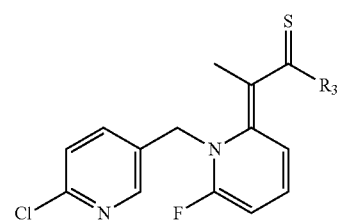 I-70 | 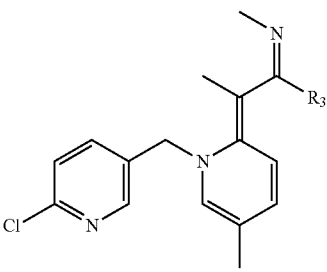 I-76 |
| 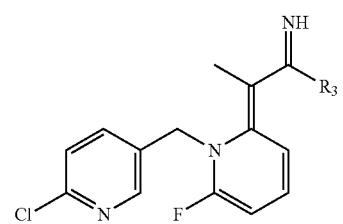 I-71 | 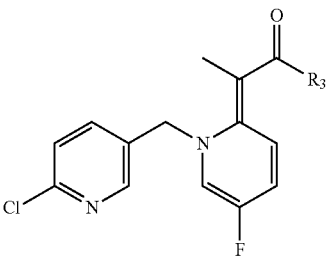 I-77 |
| 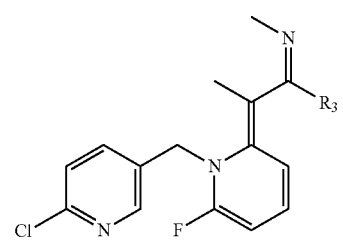 I-72 | 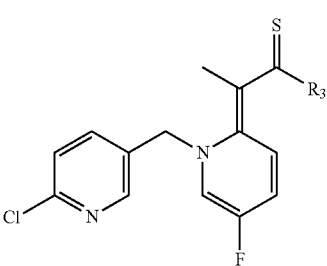 I-78 |
| 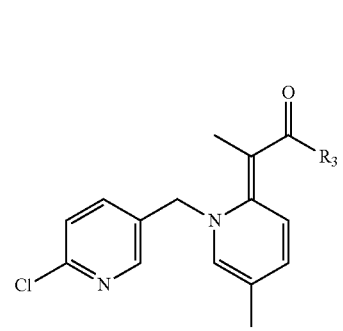 I-73 | 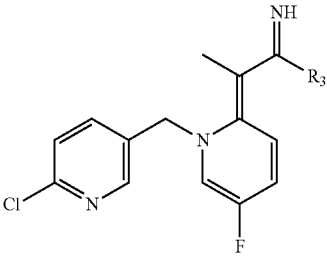 I-79 |
| 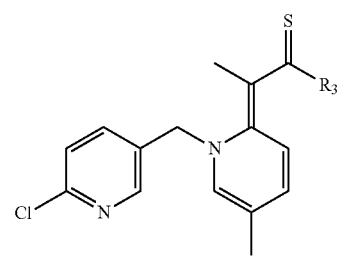 I-74 | 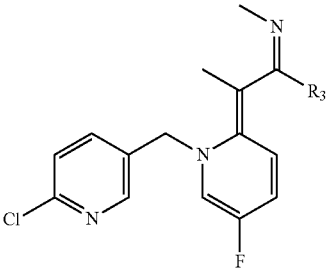 I-80 |

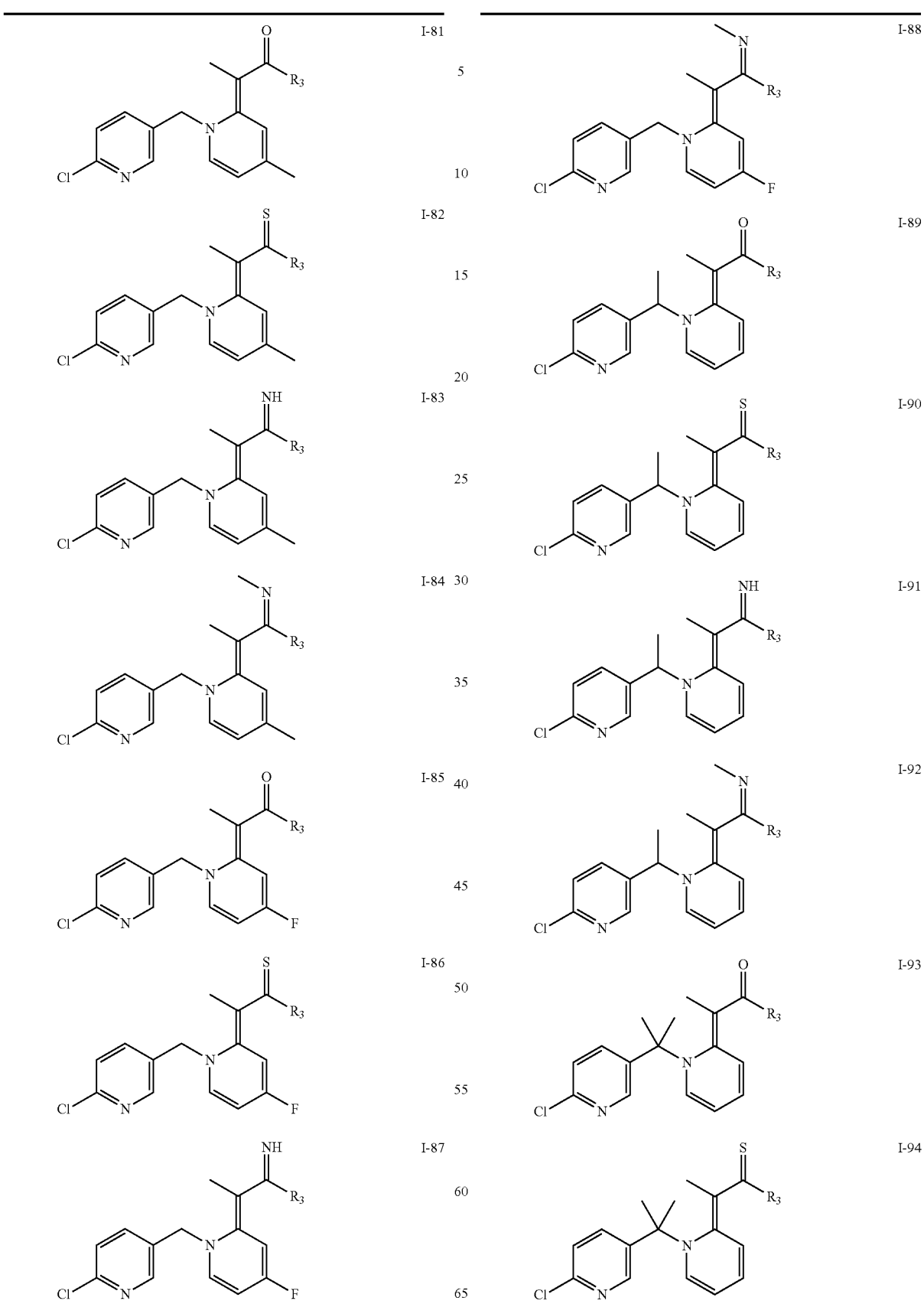

| | |
|---|---|
| 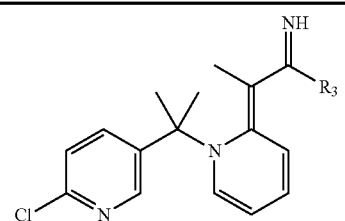 I-95 | 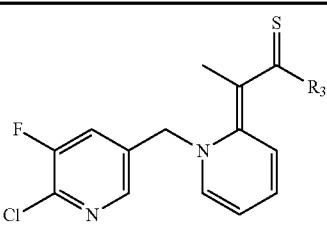 I-102 |
| 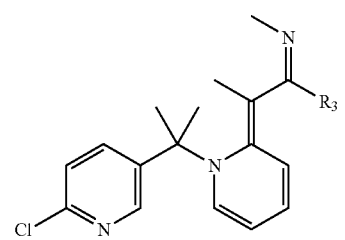 I-96 | 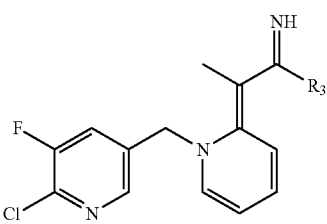 I-103 |
| 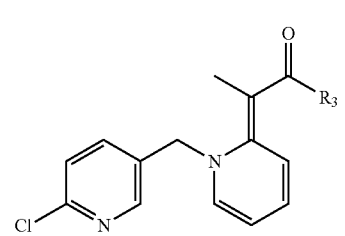 I-97 | 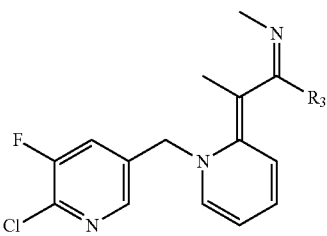 I-104 |
| 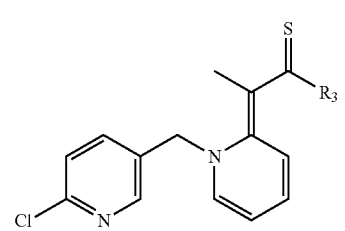 I-98 | 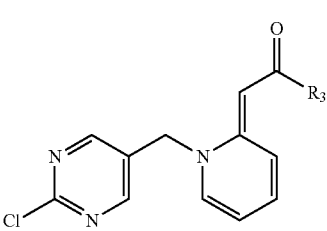 I-105 |
| 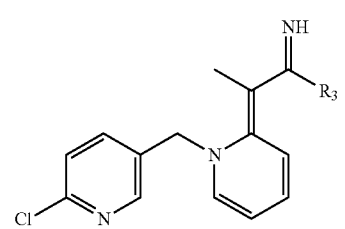 I-99 | 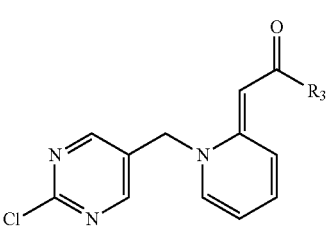 I-106 |
| 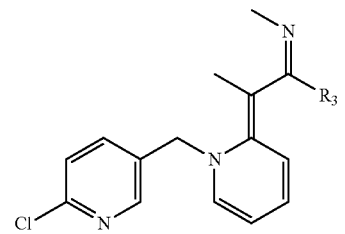 I-100 | 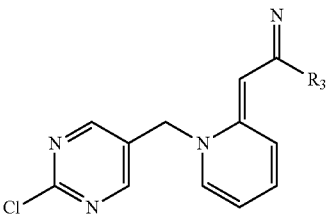 I-107 |
| 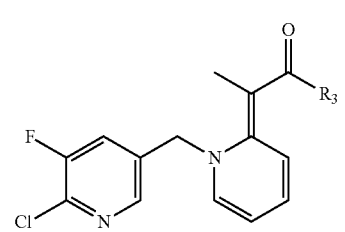 I-101 | 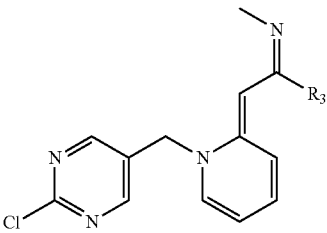 I-108 |

-continued
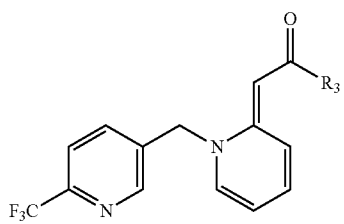 I-109
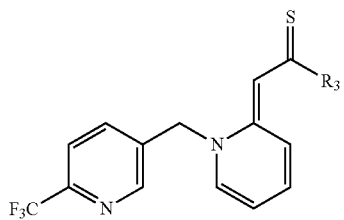 I-110
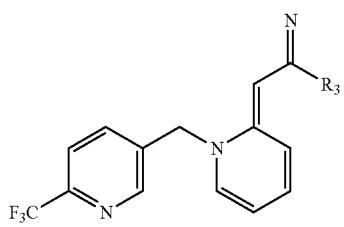 I-111
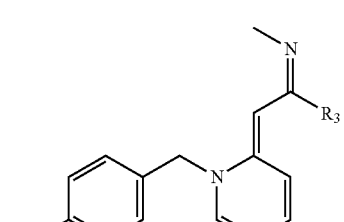 I-112
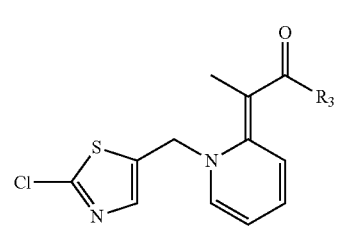 I-113
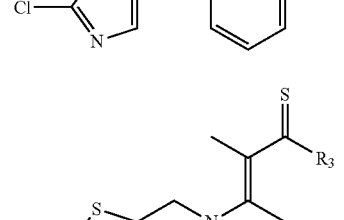 I-114
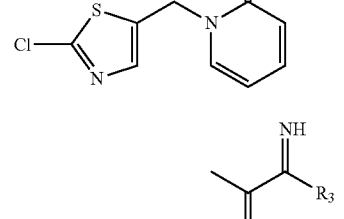 I-115
-continued
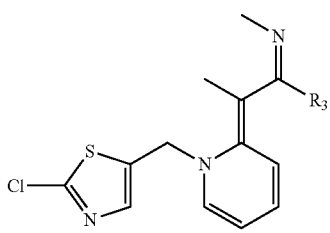 I-116
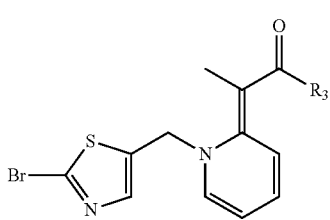 I-117
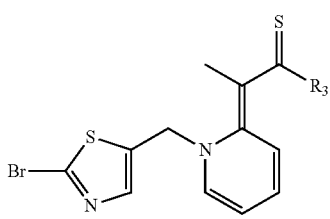 I-118
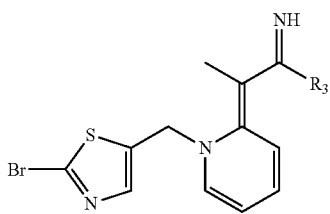 I-119
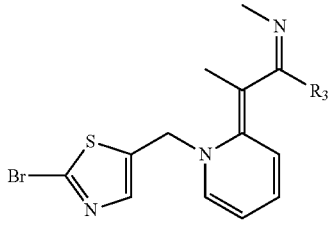 I-120
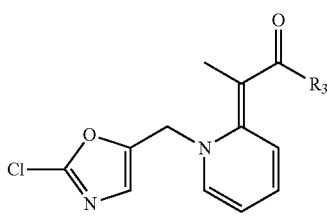 I-121
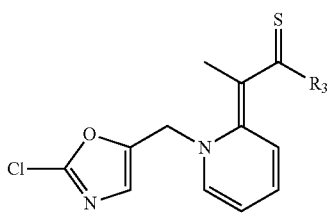 I-122

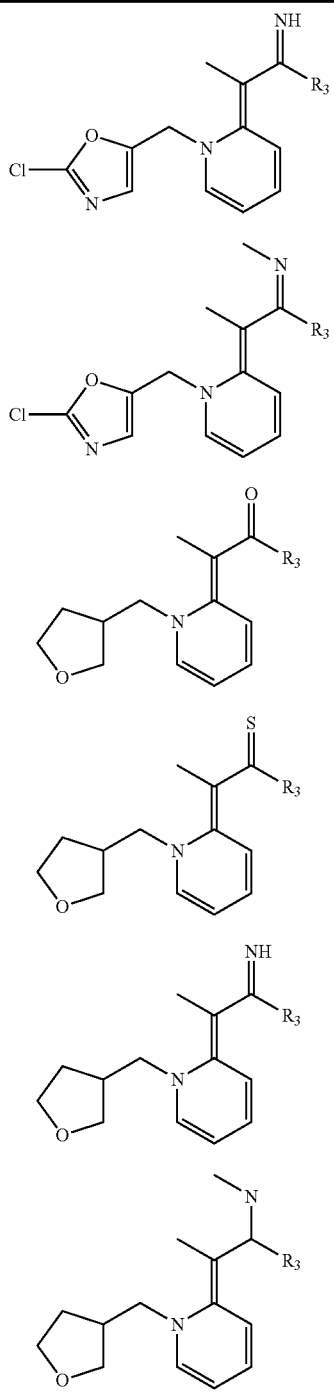

In the above mentioned 128 formulae I-1 to I-128, $R^3$ has one of the preferred meanings as given in this table C below:

TABLE C

| Compound no. | $R^3$ |
| --- | --- |
| C.I.1 | —H |
| C.I.2 | —CH$_3$ |
| C.I.3 | —CHF$_2$ |

TABLE C-continued

| Compound no. | $R^3$ |
| --- | --- |
| C.I.4 | —CF$_3$ |
| C.I.5 | —CHCl$_2$ |
| C.I.6 | —CCl$_3$ |
| C.I.7 | —C$_2$H$_5$ |
| C.I.8 | —CH=CH$_2$ |
| C.I.9 | —C$_2$F$_5$ |
| C.I.10 | —CH$_2$CF$_3$ |
| C.I.11 | —CH$_2$CHF$_2$ |
| C.I.12 | —C$_2$Cl$_5$ |
| C.I.13 | —CH$_2$CCl$_3$ |
| C.I.14 | —CH$_2$CHCl$_2$ |
| C.I.15 | —CH$_2$OH |
| C.I.16 | —CH$_2$CN |
| C.I.17 | —CH$_2$NO$_2$ |
| C.I.18 | —CH$_2$OCH$_3$ |
| C.I.19 | —CH$_2$OCF$_3$ |
| C.I.20 | —CH(CH$_3$)$_2$ |
| C.I.21 | —CH(CF$_3$)$_2$ |
| C.I.22 | —CF(CF$_3$)$_2$ |
| C.I.23 | —CH$_2$CH$_2$CH$_3$ |
| C.I.24 | —CH$_2$CH=CH$_2$ |
| C.I.25 | —CH$_2$CH=CCl$_2$ |
| C.I.26 | —CH$_2$CH=CF$_2$ |
| C.I.27 | —CH$_2$CH$_2$CH$_2$CH$_3$ |
| C.I.28 | —CH$_2$C(=O)CH$_3$ |
| C.I.29 | —CH$_2$C(=S)CH$_3$ |
| C.I.30 | —CH$_2$S(=O)CH$_3$ |
| C.I.31 | —CH$_2$S(=O)$_2$CH$_3$ |
| C.I.32 | —CH$_2$CH$_2$OCH$_3$ |
| C.I.33 | —CH$_2$CH$_2$SCH$_3$ |
| C.I.34 | 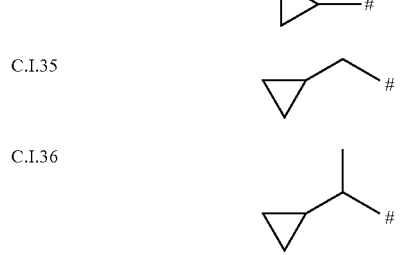 |
| C.I.35 | |
| C.I.36 | |

TABLE C-continued

| Compound no. | R³ |
|---|---|
| C.I.37 | 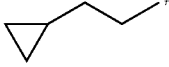 |
| C.I.38 | 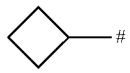 |
| C.I.39 | 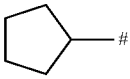 |
| C.I.40 | 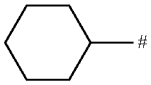 |
| C.I.41 | 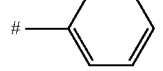 |
| C.I.42 |  |
| C.I.43 |  |
| C.I.44 |  |
| C.I.45 | 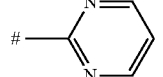 |
| C.I.46 | 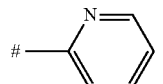 |
| C.I.47 | 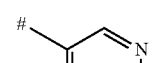 |
| C.I.48 |  |
| C.I.49 | 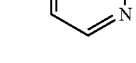 |
| C.I.50 | —(C=O)CH₃ |
| C.I.51 | —(C=S)CH₃ |
| C.I.52 | —(C=O)CF₃ |
| C.I.53 | —(C=S)CF₃ |
| C.I.54 | 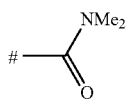 |
| C.I.55 | 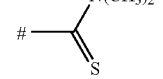 |
| C.I.56 | 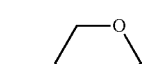 |
| C.I.57 | 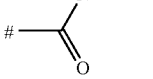 |
| C.I.58 | 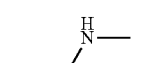 |
| C.I.59 | 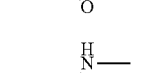 |
| C.I.60 | 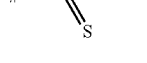 |
| C.I.61 | 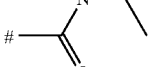 |
| C.I.62 | —NH₂ |
| C.I.63 | —NHCH₃ |
| C.I.64 | —N(CH₃)₂ |
| C.I.65 | —N(CH₂CH₃)₂ |
| C.I.66 | —NHCH₂CH₃ |
| C.I.67 | —N(CH₂CHF₂)₂ |
| C.I.68 | —OH |
| C.I.69 | —OCH₃ |
| C.I.70 | —OCF₃ |
| C.I.71 | —OCHF₂ |
| C.I.72 | —OCH₂CH₃ |
| C.I.73 | —OCH₂CHF₂ |

Examples of especially preferred compounds of formula I are given herein below.

Examples of such especially preferred compounds are compounds C.I.1 to C.I.73 of formula (I-1), wherein R³ has the meaning given in any of the lines 1 to 73 of table C.

Examples of such especially preferred compounds are compounds C.I.1 to C.I.73 of formula (I-2), wherein R³ has the meaning given in any of the lines 1 to 73 of table C.

Examples of such especially preferred compounds are compounds C.I.1 to C.I.73 of formula (I-3), wherein R³ has the meaning given in any of the lines 1 to 73 of table C.

Examples of such especially preferred compounds are compounds C.I.1 to C.I.73 of formula (I-4), wherein $R^3$ has the meaning given in any of the lines 1 to 73 of table C.

Examples of such especially preferred compounds are compounds C.I.1 to C.I.73 of formula (I-5), wherein $R^3$ has the meaning given in any of the lines 1 to 73 of table C.

Examples of such especially preferred compounds are compounds C.I.1 to C.I.73 of formula (I-6), wherein $R^3$ has the meaning given in any of the lines 1 to 73 of table C.

Examples of such especially preferred compounds are compounds C.I.1 to C.I.73 of formula (I-7), wherein $R^3$ has the meaning given in any of the lines 1 to 73 of table C.

Examples of such especially preferred compounds are compounds C.I.1 to C.I.73 of formula (I-8), wherein $R^3$ has the meaning given in any of the lines 1 to 73 of table C.

Examples of such especially preferred compounds are compounds C.I.1 to C.I.73 of formula (I-9), wherein $R^3$ has the meaning given in any of the lines 1 to 73 of table C.

Examples of such especially preferred compounds are compounds C.I.1 to C.I.73 of formula (I-10), wherein $R^3$ has the meaning given in any of the lines 1 to 73 of table C.

Examples of such especially preferred compounds are compounds C.I.1 to C.I.73 of formula (I-11), wherein $R^3$ has the meaning given in any of the lines 1 to 73 of table C.

Examples of such especially preferred compounds are compounds C.I.1 to C.I.73 of formula (I-12), wherein $R^3$ has the meaning given in any of the lines 1 to 73 of table C.

Examples of such especially preferred compounds are compounds C.I.1 to C.I.73 of formula (I-13), wherein $R^3$ has the meaning given in any of the lines 1 to 73 of table C.

Examples of such especially preferred compounds are compounds C.I.1 to C.I.73 of formula (I-14), wherein $R^3$ has the meaning given in any of the lines 1 to 73 of table C.

Examples of such especially preferred compounds are compounds C.I.1 to C.I.73 of formula (I-15), wherein $R^3$ has the meaning given in any of the lines 1 to 73 of table C.

Examples of such especially preferred compounds are compounds C.I.1 to C.I.73 of formula (I-16), wherein $R^3$ has the meaning given in any of the lines 1 to 73 of table C.

Examples of such especially preferred compounds are compounds C.I.1 to C.I.73 of formula (I-17), wherein $R^3$ has the meaning given in any of the lines 1 to 73 of table C.

Examples of such especially preferred compounds are compounds C.I.1 to C.I.73 of formula (I-18), wherein $R^3$ has the meaning given in any of the lines 1 to 73 of table C.

Examples of such especially preferred compounds are compounds C.I.1 to C.I.73 of formula (I-19), wherein $R^3$ has the meaning given in any of the lines 1 to 73 of table C.

Examples of such especially preferred compounds are compounds C.I.1 to C.I.73 of formula (I-20), wherein $R^3$ has the meaning given in any of the lines 1 to 73 of table C.

Examples of such especially preferred compounds are compounds C.I.1 to C.I.73 of formula (I-21), wherein $R^3$ has the meaning given in any of the lines 1 to 73 of table C.

Examples of such especially preferred compounds are compounds C.I.1 to C.I.73 of formula (I-22), wherein $R^3$ has the meaning given in any of the lines 1 to 73 of table C.

Examples of such especially preferred compounds are compounds C.I.1 to C.I.73 of formula (I-23), wherein $R^3$ has the meaning given in any of the lines 1 to 73 of table C.

Examples of such especially preferred compounds are compounds C.I.1 to C.I.73 of formula (I-24), wherein $R^3$ has the meaning given in any of the lines 1 to 73 of table C.

Examples of such especially preferred compounds are compounds C.I.1 to C.I.73 of formula (I-25), wherein $R^3$ has the meaning given in any of the lines 1 to 73 of table C.

Examples of such especially preferred compounds are compounds C.I.1 to C.I.73 of formula (I-26), wherein $R^3$ has the meaning given in any of the lines 1 to 73 of table C.

Examples of such especially preferred compounds are compounds C.I.1 to C.I.73 of formula (I-27), wherein $R^3$ has the meaning given in any of the lines 1 to 73 of table C.

Examples of such especially preferred compounds are compounds C.I.1 to C.I.73 of formula (I-28), wherein $R^3$ has the meaning given in any of the lines 1 to 73 of table C.

Examples of such especially preferred compounds are compounds C.I.1 to C.I.73 of formula (I-29), wherein $R^3$ has the meaning given in any of the lines 1 to 73 of table C.

Examples of such especially preferred compounds are compounds C.I.1 to C.I.73 of formula (I-30), wherein $R^3$ has the meaning given in any of the lines 1 to 73 of table C.

Examples of such especially preferred compounds are compounds C.I.1 to C.I.73 of formula (I-31), wherein $R^3$ has the meaning given in any of the lines 1 to 73 of table C.

Examples of such especially preferred compounds are compounds C.I.1 to C.I.73 of formula (I-32), wherein $R^3$ has the meaning given in any of the lines 1 to 73 of table C.

Examples of such especially preferred compounds are compounds C.I.1 to C.I.73 of formula (I-33), wherein $R^3$ has the meaning given in any of the lines 1 to 73 of table C.

Examples of such especially preferred compounds are compounds C.I.1 to C.I.73 of formula (I-34), wherein $R^3$ has the meaning given in any of the lines 1 to 73 of table C.

Examples of such especially preferred compounds are compounds C.I.1 to C.I.73 of formula (I-35), wherein $R^3$ has the meaning given in any of the lines 1 to 73 of table C.

Examples of such especially preferred compounds are compounds C.I.1 to C.I.73 of formula (I-36), wherein $R^3$ has the meaning given in any of the lines 1 to 73 of table C.

Examples of such especially preferred compounds are compounds C.I.1 to C.I.73 of formula (I-37), wherein $R^3$ has the meaning given in any of the lines 1 to 73 of table C.

Examples of such especially preferred compounds are compounds C.I.1 to C.I.73 of formula (I-38), wherein $R^3$ has the meaning given in any of the lines 1 to 73 of table C.

Examples of such especially preferred compounds are compounds C.I.1 to C.I.73 of formula (I-39), wherein $R^3$ has the meaning given in any of the lines 1 to 73 of table C.

Examples of such especially preferred compounds are compounds C.I.1 to C.I.73 of formula (I-40), wherein $R^3$ has the meaning given in any of the lines 1 to 73 of table C.

Examples of such especially preferred compounds are compounds C.I.1 to C.I.73 of formula (I-41), wherein $R^3$ has the meaning given in any of the lines 1 to 73 of table C.

Examples of such especially preferred compounds are compounds C.I.1 to C.I.73 of formula (I-42), wherein $R^3$ has the meaning given in any of the lines 1 to 73 of table C.

Examples of such especially preferred compounds are compounds C.I.1 to C.I.73 of formula (I-43), wherein $R^3$ has the meaning given in any of the lines 1 to 73 of table C.

Examples of such especially preferred compounds are compounds C.I.1 to C.I.73 of formula (I-44), wherein $R^3$ has the meaning given in any of the lines 1 to 73 of table C.

Examples of such especially preferred compounds are compounds C.I.1 to C.I.73 of formula (I-45), wherein $R^3$ has the meaning given in any of the lines 1 to 73 of table C.

Examples of such especially preferred compounds are compounds C.I.1 to C.I.73 of formula (I-46), wherein $R^3$ has the meaning given in any of the lines 1 to 73 of table C.

Examples of such especially preferred compounds are compounds C.I.1 to C.I.73 of formula (I-47), wherein $R^3$ has the meaning given in any of the lines 1 to 73 of table C.

Examples of such especially preferred compounds are compounds C.I.1 to C.I.73 of formula (I-48), wherein $R^3$ has the meaning given in any of the lines 1 to 73 of table C.

Examples of such especially preferred compounds are compounds C.I.1 to C.I.73 of formula (I-49), wherein $R^3$ has the meaning given in any of the lines 1 to 73 of table C.

Examples of such especially preferred compounds are compounds C.I.1 to C.I.73 of formula (I-50), wherein $R^3$ has the meaning given in any of the lines 1 to 73 of table C.

Examples of such especially preferred compounds are compounds C.I.1 to C.I.73 of formula (I-51), wherein $R^3$ has the meaning given in any of the lines 1 to 73 of table C.

Examples of such especially preferred compounds are compounds C.I.1 to C.I.73 of formula (I-52), wherein $R^3$ has the meaning given in any of the lines 1 to 73 of table C.

Examples of such especially preferred compounds are compounds C.I.1 to C.I.73 of formula (I-53), wherein $R^3$ has the meaning given in any of the lines 1 to 73 of table C.

Examples of such especially preferred compounds are compounds C.I.1 to C.I.73 of formula (I-54), wherein $R^3$ has the meaning given in any of the lines 1 to 73 of table C.

Examples of such especially preferred compounds are compounds C.I.1 to C.I.73 of formula (I-55), wherein $R^3$ has the meaning given in any of the lines 1 to 73 of table C.

Examples of such especially preferred compounds are compounds C.I.1 to C.I.73 of formula (I-56), wherein $R^3$ has the meaning given in any of the lines 1 to 73 of table C.

Examples of such especially preferred compounds are compounds C.I.1 to C.I.73 of formula (I-57), wherein $R^3$ has the meaning given in any of the lines 1 to 73 of table C.

Examples of such especially preferred compounds are compounds C.I.1 to C.I.73 of formula (I-58), wherein $R^3$ has the meaning given in any of the lines 1 to 73 of table C.

Examples of such especially preferred compounds are compounds C.I.1 to C.I.73 of formula (I-59), wherein $R^3$ has the meaning given in any of the lines 1 to 73 of table C.

Examples of such especially preferred compounds are compounds C.I.1 to C.I.73 of formula (I-60), wherein $R^3$ has the meaning given in any of the lines 1 to 73 of table C.

Examples of such especially preferred compounds are compounds C.I.1 to C.I.73 of formula (I-61), wherein $R^3$ has the meaning given in any of the lines 1 to 73 of table C.

Examples of such especially preferred compounds are compounds C.I.1 to C.I.73 of formula (I-62), wherein $R^3$ has the meaning given in any of the lines 1 to 73 of table C.

Examples of such especially preferred compounds are compounds C.I.1 to C.I.73 of formula (I-63), wherein $R^3$ has the meaning given in any of the lines 1 to 73 of table C.

Examples of such especially preferred compounds are compounds C.I.1 to C.I.73 of formula (I-64), wherein $R^3$ has the meaning given in any of the lines 1 to 73 of table C.

Examples of such especially preferred compounds are compounds C.I.1 to C.I.73 of formula (I-65), wherein $R^3$ has the meaning given in any of the lines 1 to 73 of table C.

Examples of such especially preferred compounds are compounds C.I.1 to C.I.73 of formula (I-66), wherein $R^3$ has the meaning given in any of the lines 1 to 73 of table C.

Examples of such especially preferred compounds are compounds C.I.1 to C.I.73 of formula (I-67), wherein $R^3$ has the meaning given in any of the lines 1 to 73 of table C.

Examples of such especially preferred compounds are compounds C.I.1 to C.I.73 of formula (I-68), wherein $R^3$ has the meaning given in any of the lines 1 to 73 of table C.

Examples of such especially preferred compounds are compounds C.I.1 to C.I.73 of formula (I-69), wherein $R^3$ has the meaning given in any of the lines 1 to 73 of table C.

Examples of such especially preferred compounds are compounds C.I.1 to C.I.73 of formula (I-71), wherein $R^3$ has the meaning given in any of the lines 1 to 73 of table C.

Examples of such especially preferred compounds are compounds C.I.1 to C.I.73 of formula (I-71), wherein $R^3$ has the meaning given in any of the lines 1 to 73 of table C.

Examples of such especially preferred compounds are compounds C.I.1 to C.I.73 of formula (I-72), wherein $R^3$ has the meaning given in any of the lines 1 to 73 of table C.

Examples of such especially preferred compounds are compounds C.I.1 to C.I.73 of formula (I-73), wherein $R^3$ has the meaning given in any of the lines 1 to 73 of table C.

Examples of such especially preferred compounds are compounds C.I.1 to C.I.73 of formula (I-74), wherein $R^3$ has the meaning given in any of the lines 1 to 73 of table C.

Examples of such especially preferred compounds are compounds C.I.1 to C.I.73 of formula (I-75), wherein $R^3$ has the meaning given in any of the lines 1 to 73 of table C.

Examples of such especially preferred compounds are compounds C.I.1 to C.I.73 of formula (I-76), wherein $R^3$ has the meaning given in any of the lines 1 to 73 of table C.

Examples of such especially preferred compounds are compounds C.I.1 to C.I.73 of formula (I-77), wherein $R^3$ has the meaning given in any of the lines 1 to 73 of table C.

Examples of such especially preferred compounds are compounds C.I.1 to C.I.73 of formula (I-78), wherein $R^3$ has the meaning given in any of the lines 1 to 73 of table C.

Examples of such especially preferred compounds are compounds C.I.1 to C.I.73 of formula (I-79), wherein $R^3$ has the meaning given in any of the lines 1 to 73 of table C.

Examples of such especially preferred compounds are compounds C.I.1 to C.I.73 of formula (I-80), wherein $R^3$ has the meaning given in any of the lines 1 to 73 of table C.

Examples of such especially preferred compounds are compounds C.I.1 to C.I.73 of formula (I-81), wherein $R^3$ has the meaning given in any of the lines 1 to 73 of table C.

Examples of such especially preferred compounds are compounds C.I.1 to C.I.73 of formula (I-82), wherein $R^3$ has the meaning given in any of the lines 1 to 73 of table C.

Examples of such especially preferred compounds are compounds C.I.1 to C.I.73 of formula (I-83), wherein $R^3$ has the meaning given in any of the lines 1 to 73 of table C.

Examples of such especially preferred compounds are compounds C.I.1 to C.I.73 of formula (I-84), wherein $R^3$ has the meaning given in any of the lines 1 to 73 of table C.

Examples of such especially preferred compounds are compounds C.I.1 to C.I.73 of formula (I-85), wherein $R^3$ has the meaning given in any of the lines 1 to 73 of table C.

Examples of such especially preferred compounds are compounds C.I.1 to C.I.73 of formula (I-86), wherein $R^3$ has the meaning given in any of the lines 1 to 73 of table C.

Examples of such especially preferred compounds are compounds C.I.1 to C.I.73 of formula (I-87), wherein $R^3$ has the meaning given in any of the lines 1 to 73 of table C.

Examples of such especially preferred compounds are compounds C.I.1 to C.I.73 of formula (I-88), wherein $R^3$ has the meaning given in any of the lines 1 to 73 of table C.

Examples of such especially preferred compounds are compounds C.I.1 to C.I.73 of formula (I-89), wherein $R^3$ has the meaning given in any of the lines 1 to 73 of table C.

Examples of such especially preferred compounds are compounds C.I.1 to C.I.73 of formula (I-90), wherein $R^3$ has the meaning given in any of the lines 1 to 73 of table C.

Examples of such especially preferred compounds are compounds C.I.1 to C.I.73 of formula (I-91), wherein $R^3$ has the meaning given in any of the lines 1 to 73 of table C.

Examples of such especially preferred compounds are compounds C.I.1 to C.I.73 of formula (I-92), wherein $R^3$ has the meaning given in any of the lines 1 to 73 of table C.

Examples of such especially preferred compounds are compounds C.I.1 to C.I.73 of formula (I-93), wherein $R^3$ has the meaning given in any of the lines 1 to 73 of table C.

Examples of such especially preferred compounds are compounds C.I.1 to C.I.73 of formula (I-94), wherein $R^3$ has the meaning given in any of the lines 1 to 73 of table C.

Examples of such especially preferred compounds are compounds C.I.1 to C.I.73 of formula (I-95), wherein $R^3$ has the meaning given in any of the lines 1 to 73 of table C.

Examples of such especially preferred compounds are compounds C.I.1 to C.I.73 of formula (I-96), wherein $R^3$ has the meaning given in any of the lines 1 to 73 of table C.

Examples of such especially preferred compounds are compounds C.I.1 to C.I.73 of formula (I-97), wherein $R^3$ has the meaning given in any of the lines 1 to 73 of table C.

Examples of such especially preferred compounds are compounds C.I.1 to C.I.73 of formula (I-98), wherein $R^3$ has the meaning given in any of the lines 1 to 73 of table C.

Examples of such especially preferred compounds are compounds C.I.1 to C.I.73 of formula (I-99), wherein $R^3$ has the meaning given in any of the lines 1 to 73 of table C.

Examples of such especially preferred compounds are compounds C.I.1 to C.I.73 of formula (I-100), wherein $R^3$ has the meaning given in any of the lines 1 to 73 of table C.

Examples of such especially preferred compounds are compounds C.I.1 to C.I.73 of formula (I-101), wherein $R^3$ has the meaning given in any of the lines 1 to 73 of table C.

Examples of such especially preferred compounds are compounds C.I.1 to C.I.73 of formula (I-102), wherein $R^3$ has the meaning given in any of the lines 1 to 73 of table C.

Examples of such especially preferred compounds are compounds C.I.1 to C.I.73 of formula (I-103), wherein $R^3$ has the meaning given in any of the lines 1 to 73 of table C.

Examples of such especially preferred compounds are compounds C.I.1 to C.I.73 of formula (I-104), wherein $R^3$ has the meaning given in any of the lines 1 to 73 of table C.

Examples of such especially preferred compounds are compounds C.I.1 to C.I.73 of formula (I-105), wherein $R^3$ has the meaning given in any of the lines 1 to 73 of table C.

Examples of such especially preferred compounds are compounds C.I.1 to C.I.73 of formula (I-106), wherein $R^3$ has the meaning given in any of the lines 1 to 73 of table C.

Examples of such especially preferred compounds are compounds C.I.1 to C.I.73 of formula (I-107), wherein $R^3$ has the meaning given in any of the lines 1 to 73 of table C.

Examples of such especially preferred compounds are compounds C.I.1 to C.I.73 of formula (I-108), wherein $R^3$ has the meaning given in any of the lines 1 to 73 of table C.

Examples of such especially preferred compounds are compounds C.I.1 to C.I.73 of formula (I-109), wherein $R^3$ has the meaning given in any of the lines 1 to 73 of table C.

Examples of such especially preferred compounds are compounds C.I.1 to C.I.73 of formula (I-110), wherein $R^3$ has the meaning given in any of the lines 1 to 73 of table C.

Examples of such especially preferred compounds are compounds C.I.1 to C.I.73 of formula (I-111), wherein $R^3$ has the meaning given in any of the lines 1 to 73 of table C.

Examples of such especially preferred compounds are compounds C.I.1 to C.I.73 of formula (I-112), wherein $R^3$ has the meaning given in any of the lines 1 to 73 of table C.

Examples of such especially preferred compounds are compounds C.I.1 to C.I.73 of formula (I-113), wherein $R^3$ has the meaning given in any of the lines 1 to 73 of table C.

Examples of such especially preferred compounds are compounds C.I.1 to C.I.73 of formula (I-114), wherein $R^3$ has the meaning given in any of the lines 1 to 73 of table C.

Examples of such especially preferred compounds are compounds C.I.1 to C.I.73 of formula (I-115), wherein $R^3$ has the meaning given in any of the lines 1 to 73 of table C.

Examples of such especially preferred compounds are compounds C.I.1 to C.I.73 of formula (I-116), wherein $R^3$ has the meaning given in any of the lines 1 to 73 of table C.

Examples of such especially preferred compounds are compounds C.I.1 to C.I.73 of formula (I-117), wherein $R^3$ has the meaning given in any of the lines 1 to 73 of table C.

Examples of such especially preferred compounds are compounds C.I.1 to C.I.73 of formula (I-118), wherein $R^3$ has the meaning given in any of the lines 1 to 73 of table C.

Examples of such especially preferred compounds are compounds C.I.1 to C.I.73 of formula (I-119), wherein $R^3$ has the meaning given in any of the lines 1 to 73 of table C.

Examples of such especially preferred compounds are compounds C.I.1 to C.I.73 of formula (I-120), wherein $R^3$ has the meaning given in any of the lines 1 to 73 of table C.

Examples of such especially preferred compounds are compounds C.I.1 to C.I.73 of formula (I-121), wherein $R^3$ has the meaning given in any of the lines 1 to 73 of table C.

Examples of such especially preferred compounds are compounds C.I.1 to C.I.73 of formula (I-122), wherein $R^3$ has the meaning given in any of the lines 1 to 73 of table C.

Examples of such especially preferred compounds are compounds C.I.1 to C.I.73 of formula (I-123), wherein $R^3$ has the meaning given in any of the lines 1 to 73 of table C.

Examples of such especially preferred compounds are compounds C.I.1 to C.I.73 of formula (I-124), wherein $R^3$ has the meaning given in any of the lines 1 to 73 of table C.

Examples of such especially preferred compounds are compounds C.I.1 to C.I.73 of formula (I-125), wherein $R^3$ has the meaning given in any of the lines 1 to 73 of table C.

Examples of such especially preferred compounds are compounds C.I.1 to C.I.73 of formula (I-126), wherein $R^3$ has the meaning given in any of the lines 1 to 73 of table C.

One preferred isomer of compounds of formula (I) of the present invention, especially with the preferred variables outlined above, is the E-isomer.

One preferred isomer of compounds of formula (I) of the present invention, especially with the preferred variables outlined above, is the Z-isomer.

For example, Compound C.I.4 of formula I-33 would be preferred according to the following E/Zisomers:

E-isomer

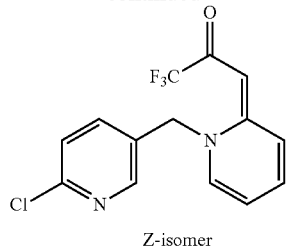

Z-isomer

Moreover, the meanings mentioned for those individual variables in the tables and further above are per se, independently of the combination in which they are mentioned, a particularly preferred embodiment of the substituents in question.

Preparation Methods

Compound of formula (I) according to the present invention can be prepared e.g. according the preparation methods and preparation schemes as described below.

Compounds of formula (I) according to the present invention can be prepared by standard methods of organic chemistry e.g. by the preparation methods and preparation schemes as described below. The definitions of Het, $R^1$, $R^2$, $R^4$ and $R^4$ of the molecular structures given in the schemes are as defined above. Room temperature means a temperature range between about 20 and 25° C.

An examples of a general method for the preparation of compounds of formula (I) is shown below in Scheme A. Thus, construction of pyridinylidene element present in compounds of formula (I) can be achieved, for example, by alkylation of the exocyclic methyl group in pyridinium precursors of formula 3 with a reagent of formula 4. The transformation is preferably carried out in polar solvents such as acetonitrile, acetone, dichloromethane, tetrahydrofurane, N,N-dimethylformamide, a $C_1$-$C_6$ alcohol or water optionally in the presence of a base such as a carbonate, tertiary amine base or an alkali metal hydride, hydroxide or alkoxide at temperatures ranging between room temperature and the reflux temperature of the solvent. Representative reaction conditions for the alkylation of pyridinium precursors analogous to formula 3 are given in J. Het. Chem. 1995, 32(2), 391-394. The synthesis of precursors of formula 3 can be achieved by alkylation of the pyridine nitrogen in compounds of formula 1. The transformation is preferably carried out in polar solvents such as acetonitrile, acetone, tetrahydrofuran, N,N-dimethylformamide, a $C_1$-$C_6$ alcohol or water or in an inert solvent such as benzene, toluene or xylene at temperatures ranging between room temperature and the reflux temperature of the solvent. Representative reaction conditions for the N-alkylation of 2-substituted pyridines are given in US2005/009954 and Tetrahedron 2005, 61(43), 10331-10337. Examples of suitable leaving groups (LG) in formulae 2 and 4 include, but are not limited to, halogen, alkyl sulfonate or haloalkyl sulfonate.

Scheme A:

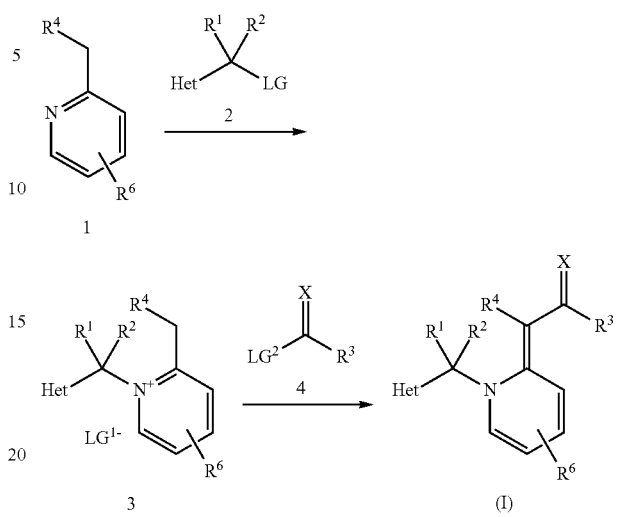

A representative preparation method for (1E)-1-[1-[(6-chloro-3-pyridyl)methyl]-2-pyridylidene]propan-2-one (Ia) representing a substructure of compounds of formula I-33 with $R^3$ being $CH_3$ is shown in Scheme B. A solution of 2-methyl-pyridine (1 equivalent) and 2-chloro-5-(iodomethyl)pyridine (1 equivalent) that is prepared from 2-chloro-5-(chloromethyl)pyridine according to US2005/0228027 in acetonitrile is stirred at reflux temperature for 12 h. The solvent is evaporated under reduced pressure to give compound 7. Similar to the procedure described in J. Heterocyclic Chem. 1995, 32, 391-394 the crude pyridinium iodide 7 (1 equivalent) is dissolved in $H_2O$ and $CH_2Cl_2$ (1:2 mixture) and under vigorous stirring acetyl chloride (2 equivalents) is added. A NaOH-solution (25% in $H_2O$) is added over 5 minutes and stirring is continued for 30 minutes. The reaction mixture is extracted three times with dichloromethane and the combined organic extracts are dried with $Na_2SO_4$.

Scheme B:

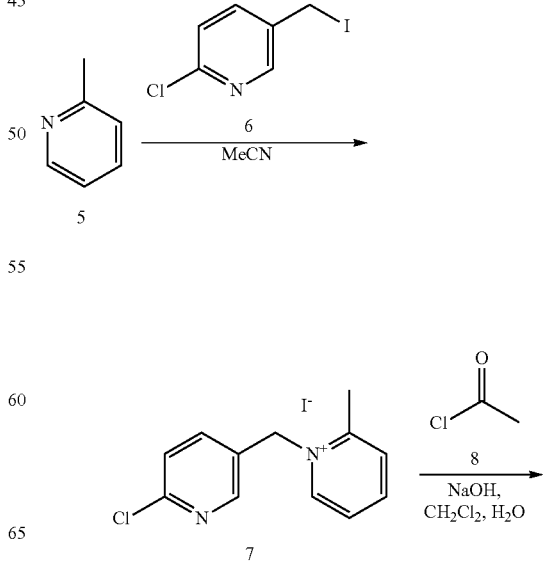

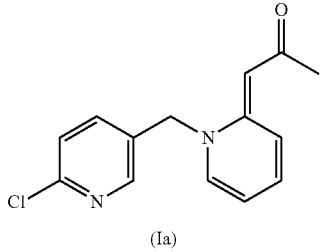

(Ia)

If individual compounds cannot be prepared via the above-described routes, they can be prepared by derivatization of other compounds (I) or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Pests

The compounds of the formula I, and their salts are in particular suitable for efficiently controlling arthropodal pests such as arachnids, myriapedes and insects as well as nematodes.

The compounds of the formula I are especially suitable for efficiently combating the following pests:

Insects from the order of the lepidopterans (*Lepidoptera*), for example *Agrotis ypsilon, Agrotis segetum, Alabama argilacea, Anticarsia gemmatalis, Argyresthia conjugella, Autographa gamma, Bupalus piniarius, Cacoeda murnana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeela, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis fiammea, Peciinophora gossypiella, Peridroma sauda, Phalera bucephala, Phthonmaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (*Coleoptera*), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vesperinus, Crioceris asparagi; Ctenicera* ssp., *Diabrotica longicornis, Diabrotica semipundata, Diabrotica 12-punctata Diabrotica speciosa, Diabrotica virgifera, Epilachna varivestis, Epitrix hirtipennis, Eutinobothrus brasilensis, Hylobius abietis, Hypera brunneipennis, Hypera postica, Ips typographus, Lema bilineata, Lema melanopus, Leptinotarsa decemlineata, Limonius calfornicus, Lissorhoptrus oryzophilus, Melanotus communis, Meligethes aeneus, Melolontha hippocastani; Melolontha melolontha, Oulema oryzae, Otiorrhynchus sulcatus, Otiorrhynchus ovatus, Phaedon cochleariae, Phyllobius pyri; Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (*Diptera*), e.g. *Aedes aegypti; Aedes albopictus Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinodes, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (*Thysanoptera*), e.g. *Dichromothrips corbetti, Dichromothrips* ssp., *Frankinella fusca, Frankiniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (Blattaia-Blattodea), e.g. *Blattella germanica, Blattella asahinae, Periplaneta americana, Periplaneta japonica, Periplaneta brunnea, Penplaneta fulgginosa, Periplaneta australasiae,* and *Blatta orientalis;* bugs, aphids, leafhoppers, whiteflies, scale insects, cicadas (*Hemiptera*), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis,*

*Aphidula nasturtii, Aphis fabae, Aphis forbesi, Aphis pomi, Aphis gossypiim, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosoani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mai, Schizaphis graminum, Schizoneura lanuginosa, Sitobion avenae, Trialeurodes vaporariorum, Toxoptera aurantiiand, Viteus vitifolii, Cimex lectularius, Cimax hemipterus, Reduvius senilis, Triatoma* spp., and *Arilus critatus;* ants, bees, wasps, sawflies (*Hymenoptera*), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (*Othoptera*), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hierogyphus daganensis, Kraussaria angulifera, Calliptamus italicus, Chortoicetes terminifera,* and *Locustana pardalina;* arachnoidea, such as arachnids (*Acarina*), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi; Sarcoptes scabiei* and *Eriophyidae* spp. such as *Aculus schlechtendali, Phyllocoptrata oleivora* and *Enophyes sheldoni, Tarsonemidae* spp. such as *Phytonemus pallidus* and *Polyphagotarsonemus latus, Tenuipalpidae* spp. such as *Brevipalpus phoenicis, Tetranychidae* spp. such as *Tetranychus cinnabannus, Tetranychus kanzawai, Tetranychus pacficus, Tetranychus telarius* and *Tetranychus urticae, Panonychus ulmi, Panonychus citri,* and *Oligonychus pratensis,* Araneida, e.g. *Latrodedus mactans,* and *Loxosceles redusa,* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma sacchanna* and *Thermobia domestica,* centipedes (Chiopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capits, Pediculus humanus oparis, Pthirus pubis, Haematopinus eurystemus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochensis* and other *Globodera* species; *Heterodera avenae, Heterodera glycines, Heterodera schachii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trirchodorus primtivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the formula I and their salts are also useful for controlling arachnids (Arachnoidea), such as acarians (Acarina), e.g. of the families Argasidae, Ixodidae and Sarcoptdae, such as *Amblyomma americanum, Amblyomma vaniegatum, Argas persicus, Boophilus annulatus, Boophilus decoloratus, Boophilus microplus, Dermacentor silvarum, Hyalomma truncatum, Ixodes richius, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni, Tarsonemidae* spp. such as *Phytonemus pallidus* and *Polyphagotarsonemus latus, Tenuipalpidae* spp. such as *Brevipalpus phoenics; Tetranychidae* spp. such as *Tetranychus cinnabannus, Tetranychus kanzawa, Tetranychus pacificus, Tetranychus telarius* and *Tetranychus urticae, Panonychus ulmi, Panonychus citri,* and *oligonychus pratensis.*

Compounds of the formula I are particularly useful for controlling insects, preferably sucking or piercing insects such as insects from the genera *Thysanoptera, Diptera* and *Hemiptera*, in particular the following species:

*Thysanoptera: Frankiniella fusca, Frankliniella occidentalis, Frankliniella tritici, Scirtothrips citri; Thrips oryzae, Thrips palmi* and *Thrips tabaci*,

*Diptera*, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nignpalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhodalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

*Hemiptera*, in particular aphids: *Acyrthosiphon onobrychis, Adelges laricis, Aphidula nasturtii, Aphis fabae, Aphis forbesi, Aphis pomi; Aphis gossypii, Aphis grossulanae, Aphis schneideri; Aphis spiraecola, Aphis sambuci, Acyrthosiphon pisum, Aulacorthum solani, Brachycaudus cardui, Brachycaudus helichrysi; Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri; Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii*.

Compounds of the formula I are particularly useful for controlling insects of the orders *Hemiptera* and *Thysanoptera*.

Formulations

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineers Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:

solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal Suitable thickeners are compounds which confer a pseudo-plastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:
1. Products for dilution with water. For seed treatment purposes, such products may be applied to the seed diluted or undiluted.
A) Water-Soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.
B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.
C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.
D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.
E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.
F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides, categorized and classified according to the Insecticde Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemetonmethyl, parathion, parathionmethyl, phenthoate, phorate, phosalone, phosmet, phosphamidon, phoxim, pirimiphosmethyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example

M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21 B rotenone;

M.22 Voltage-dependent sodium channel blockers, for example

M.22A indoxacarb, or M.22B metaflumizone;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methyl-sulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methyl-sulfonylethyl)phthalamid, or the compound M.28.3: 3-bromo-N-{2-bromo-4-chloro-6-[(1-cyclopropyl-ethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlo-rpyridin-2-yl)-1H-pyrazol-5-yl]carbonyl}amino)ben-zoyl]-1,2-dimethylhydrazinecarboxylate; or a compound selected from M.28.5 a) to M.28.5h):

M.28.5 a) N-[4,6-dichloro-2-[(diethyl-lambda-4-sulfa-nylidene)carbamoyl]-phenyl]-2-(3-chloro-2-pyridyl)-5-(trifluoromethyl)pyrazole-3-carboxamide;

M.28.5 b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5 c) N-[4-chloro-2-[(di-2-propyl-lambda-4-sulfa-nylidene)carbamoyl]-6-methyl-phenyl]-2-(3-chloro-2-py-ridyl)-5-(trifluoromethyl)pyrazole-3-carboxamide;

M.28.5 d) N-[4,6-dichloro-2-[(di-2-propyl-lambda-4-sulfa-nylidene)carbamoyl]-phenyl]-2-(3-chloro-2-pyridyl)-5-(trifluoromethyl)pyrazole-3-carboxamide;

M.28.5 e) N-[4,6-dichloro-2-[(diethyl-lambda-4-sulfa-nylidene)carbamoyl]-phenyl]-2-(3-chloro-2-pyridyl)-5-(difluoromethyl)pyrazole-3-carboxamide;

M.28.5 f) N-[4,6-dibromo-2-[(di-2-propyl-lambda-4-sulfa-nylidene)carbamoyl]-phenyl]-2-(3-chloro-2-pyridyl)-5-(trifluoromethyl)pyrazole-3-carboxamide;

M.28.5 g) N-[4-chloro-2-[(di-2-propyl-lambda-4-sulfa-nylidene)carbamoyl]-6-cyano-phenyl]-2-(3-chloro-2-py-ridyl)-5-(trifluoromethyl)pyrazole-3-carboxamide;

M.28.5 h) N-[4,6-dibromo-2-[(diethyl-lambda-4-sulfa-nylidene)carbamoyl]-phenyl]-2-(3-chloro-2-pyridyl)-5-(trifluoromethyl)pyrazole-3-carboxamide;

M.UN insecticidal active compounds of unknown or uncertain mode of action, as for example azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, or the compound M. UN.1: 4-[5-(3,5-Dichloro-phenyl)-5-trifluoromethyl-4,5-dihydro-isoxazol-3-yl]-2-methyl-N-[(2,2,2-trifluoro-eth-ylcarbamoyl)-methyl]-benzamide, or the compound M. UN.2: cyclopropaneacetic acid, 1,1'-[(3S,4R,4aR,6S,6aS, 12R,12aS,12bS)-4-[[(2-cyclopropylacetyl)oxy]methyl]-1,3,4,4a,5,6,6a,12,12a,12b-decahydro-12-hydroxy-4,6a, 12b-trimethyl-11-oxo-9-(3-pyridinyl)-2H,11H-naphtho [2,1-b]pyrano[3,4-e]pyran-3,6-diyl]ester, or the compound M. UN.3: 11-(4-chloro-2,6-dimethylphenyl)-12-hydroxy-1, 4-dioxa-9-azadispiro[4.2.4.2]-tetradec-11-en-10-one, or the compound M. UN.4: 3-(4'-fluoro-2,4-dimethylbiphenyl-3-yl)-4-hy-droxy-8-oxa-1-azaspiro[4.5]dec-3-en-2-one, or the compound M. UN.5: 1-[2-fluoro-4-methyl-5-[(2,2,2-trifluoroethyl) sulfinyl]phenyl]-3-(trifluoromethyl)-1H-1,2,4-triazole-5-amine, or actives on basis of *bacillus firmus* (Votivo, I-1582).

The commercially available compounds of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The isoxazoline compound M. UN.1 has been described in WO2005/085216. The pyripyropene derivative M. UN.2 has been described in WO 2006/129714. The spiroketal-substituted cyclic ketoenol derivative M. UN.3 is known from WO2006/089633 and the biphenyl-substituted spirocyclic ketoenol derivative M. UN.4 from WO2008/067911. Triazoylphenylsulfide like M. UN.5 have been described in WO2006/043635 and biological control agents on basis of *bacillus firmus* in WO2009/124707.

The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5 a) to M.28.5 h) can be prepared as described in WO 2007/006670, PCT/EP2012/065650 and PCT/EP2012/065651.

In another embodiment of the invention, the compounds of formula (I), or their stereoisomers, salts, tautomers and N-oxides, may also be applied with fungicides as compound II.

The following list F of active substances, in conjunction with which the compounds according to the invention can be used, is intended to illustrate the possible combinations but does not limit them:

F.I) Respiration Inhibitors
F.I-1) Inhibitors of complex III at Qo Site:
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxyacrylic acid methyl ester and 2 (2-(3-(2,6-dichlorophenyl)-1-methyl-allylideneaminooxymethyl)-phenyl)-2-methoxyimino-N methylacetamide;
oxazolidinediones and imidazolinones: famoxadone, fenamidone;

F.I-2) Inhibitors of complex II (e.g. carboxamides):
carboxanilides: benodanil, benzovindiflupyr, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide (fluxapyroxad), N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, 3-(difluoromethyl)-1-methyl-N-(1,1,3-trimethylindan-4-yl) pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

F.I-3) Inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I, uncouplers) diflumetorim; (5,8-difluoroquinazolin-4-yl)-{2-[2-fluoro-4-(4-trifluoromethylpyridin-2-yloxy)-phenyl]-ethyl}-amine; tecnazen; ametoctradin; silthiofam; nitrophenyl derivates: binapacryl, dinobuton, dinocap, fluazinam, ferimzone, nitrthalisopropyl,
and including organometal compounds: fentin salts, such as fentin-acetate, fentin chloride or fentin hydroxide;

F.II) Sterol Biosynthesis Inhibitors (SBI Fungicides)
F.II-1) C14 demethylase inhibitors (DMI fungicides, e.g. triazoles, imidazoles)
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S,3R)-3-(2-chlorophenyl)-2-(2,4-difluorophenyl)-oxiranylmethyl]-2H-[1,2,4]triazole-3-thiol;
imidazoles: imazalil, pefurazoate, oxpoconazole, prochloraz, triflumizole;
pyrimidines, pyridines and piperazines: fenarimol, nuarimol, pyrifenox, triforine, 1-[rel-(2S;3R)-3-(2-chlorophenyl)-2-(2,4-difluorophenyl)-oxiranylmethyl]-5-thiocyanato-1H-[1,2,4]triazole, 2-[rel(2S;3R)-3-(2-chlorophenyl)-2-(2,4-difluorophenyl)-oxiranylmethyl]-2H-[1,2,4]triazole-3-thiol;

F.II-2) Delta14-reductase inhibitors (Amines, e.g. morpholines, piperidines)
morpholines: aldimorph, dodemorph, dodemorph-acetate, fenpropimorph, tridemorph;
piperidines: fenpropidin, piperalin; spiroketalamines: spiroxamine;

F.II-3) Inhibitors of 3-keto reductase: hydroxyanilides: fenhexamid;

F.III) Nucleic Acid Synthesis Inhibitors
F.III-1) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;
F.III-2) DNA topisomerase inhibitors: oxolinic acid;
F.III-3) Nucleotide metabolism (e.g. adenosin-deaminase), hydroxy(2-amino)-pyrimidines: bupirimate;
F.IV) Inhibitors of Cell Division and or Cytoskeleton
F.IV-1) Tubulin inhibitors: benzimidazoles and thiophanates: benomyl, carbendazim, fuberidazole, thiabendazole, thiophanate-methyl;
triazolopyrimidines: 5-chloro-7 (4-methylpiperidin-1-yl)-6-(2,4,6-trifluorophenyl)-[1,2,4]triazolo[1,5 a]pyrimidine;
F.IV-2) Other cell division inhibitors
benzamides and phenyl acetamides: diethofencarb, ethaboxam, pencycuron, fluopicolide, zoxamide;
F.IV-3) Actin inhibitors: benzophenones: metrafenone; pyriofenone;
F.V) Inhibitors of Amino Acid and Protein Synthesis
F.V-1) Methionine synthesis inhibitors (anilino-pyrimidines) anilino-pyrimidines: cyprodinil, mepanipyrim, nitrapyrin, pyrimethanil;
F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;
F.VI) Signal Transduction Inhibitors
F.VI-1) MAP/Histidine kinase inhibitors (e.g. anilino-pyrimidines)
dicarboximides: fluoroimid, iprodione, procymidone, vinclozolin;
phenylpyrroles: fenpiclonil, fludioxonil;
F.VI-2) G protein inhibitors: quinolines: quinoxyfen;
F.VII) Lipid and Membrane Synthesis Inhibitors
F.VII-1) Phospholipid biosynthesis inhibitors
organophosphorus compounds: edifenphos, iprobenfos, pyrazophos;
dithiolanes: isoprothiolane;
F.VII-2) Lipid peroxidation: aromatic hydrocarbons: dicloran, quintozene, tecnazene, tolclofosmethyl, biphenyl, chloroneb, etridiazole;
F.VII-3) Carboxyl acid amides (CAA fungicides)
cinnamic or mandelic acid amides: dimethomorph, flumorph, mandipropamid, pyrimorph;
valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;
F.VII-4) Compounds affecting cell membrane permeability and fatty acids:
1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamates: propamocarb, propamocarbhydrochlorid,
F.VII-5) fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;
F.VIII) Inhibitors with Multi Site Action
F.VIII-1) Inorganic active substances: Bordeaux mixture, copper acetate, copper hydroxide, copper oxychloride, basic copper sulfate, sulfur;
F.VIII-2) Thio- and dithiocarbamates: ferbam, mancozeb, maneb, metam, methasulphocarb, metiram, propineb, thiram, zineb, ziram;
F.VIII-3) Organochlorine compounds (e.g. phthalimides, sulfamides, chloronitriles):
anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitrophenyl)-N-ethyl-4-methyl-benzenesulfonamide;
F.VIII-4) Guanidines and other: guanidine, dodine, dodine free base, guazatine, guazatineacetate, iminoctadine, iminoctadine-triacetate, iminoctadine-tris(albesilate), 2,6-dimethyl-1H,5H-[1,4]dithiino[2,3-c:5,6-c']dipyrrole-1,3,5,7(2H,6H)-tetraone;
F.VIII-5) Ahtraquinones: dithianon;
F.IX) Cell Wall Synthesis Inhibitors
F.IX-1) Inhibitors of glucan synthesis: validamycin, polyoxin B;
F.IX-2) Melanin synthesis inhibitors: pyroquilon, tricyclazole, carpropamid, dicyclomet, fenoxanil;
F.X) Plant Defence Inducers
F.X-1) Salicylic acid pathway: acibenzolar-S-methyl;
F.X-2) Others: probenazole, isotianil, tiadinil, prohexadione-calcium;
phosphonates: fosetyl, fosetyl-aluminum, phosphorous acid and its salts;
F.XI) Unknown mode of action: bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, oxincopper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)acetyl] piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;
F.XI) Growth regulators: abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological Control Agents

*Ampelomyces quisqualis* (e.g. AQ 10® from Intrachem Bio GmbH & Co. KG, Germany), *Aspergillus flavus* (e.g. AFLA-GUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRLNr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIO-CURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTI-BOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ).

The commercially available compounds II of the group F listed above may be found in The Pesticide Manual, 15th Edition, C. D. S. Tomlin, British Crop Protection Council (2011) among other publications. Their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EPA 141 317; EP-A 152 031; EP-A 226 917; EPA 243 970; EPA 256 503; EP-A 428 941; EP-A 532 022; EP-A 1 028 125; EP-A 1 035 122; EPA 1 201 648; EPA 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

Applications

The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of *durum* and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 Jul.-Aug. 17(4):720-8., Protein Eng Des Sel. 2004 January; 17(1):57-66, Nat Protoc. 2007; 2(5):1225-35, Curr Opin Chem Biol. 2006 October; 10(5):487-91. Epub 2006 Aug. 28, Biomaterials. 2001 March; 22(5):405-17, Bioconjug Chem. 2005 Jan.-Feb. 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus Bacillus, particularly from Bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insectspecific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for ex-ample, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EPA 0 392 225), plant disease resistance genes (for example potato cultivars, which express resistance genes acting against Phytophthora infestans derived from the mexican wild potato Solanum bulbocastanum) or T4-lysozym (e.g. potato cultivars capable of synthesizing these proteins with increased resistance against bacteria such as Erwinia amylvora). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedling's roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably aa method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting. The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of *durum* and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or the enantiomers or veterinarily acceptable salts thereof are in particular also suitable for being used for combating parasites in and on animals.

An object of the present invention is therfore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ectoand/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (*Diptera*), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellana, Chrysops discalis, Chrysops silacea, Chrysops atlanticus, Cochliompa hominivorax, Cordylobia anthropophaga, Culicoides furens, Culex pipiens, Culex nigripalpus, Culex quinque-fasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens,*

*Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoi-Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (*Ixodida*), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterofichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius sendis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and lschnocerina), e.g. *Trirnenopon* spp., *Menopon* spp., *Trinoton* spp., *Bovicola* spp., *Werneckiella* spp., *Lepikentron* spp., *Trichodectes* spp., and *Felicola* spp, Roundworms *Nematoda*:

Wipeworms and Trichinosis (*Trichosyringida*), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma resale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascanis leonine, Skrjabinema* spp., and *Oxyuris equi*, Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp., *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski,* *Clonorchis sinensis, Schistosoma* spp., *Trichobilharzia* spp., *Alana alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders *Diptera, Siphonaptera* and *Ixodida.*

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms *nematoda*, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and nbutanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

EXAMPLES

The present invention is now illustrated in further details by the following examples, without imposing any limitation thereto.

S. Synthesis Examples

Synthesis Example S.1

(3E)-3-[1-[(6-chloro-3-pyridyl)methyl]-2-pyridylidene]-1,1,1-trifluoro-propan-2-one

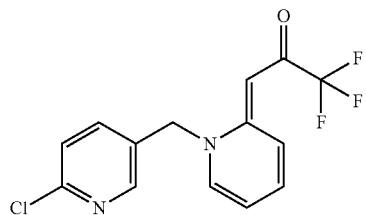

E-1

To a solution of 1,1,1-trifluoro-3-(2-pyridyl)propan-2-one (0.5 g, 2.64 mmol), that was synthesized following a literature procedure (Heterocycles 1998, 48, 2103.2109), in $CH_3CN$ (20 mL) were added 2-chloro-5-(chloromethyl)pyridine (0.64 g, 3.96 mmol) and $K_2CO_3$ (0.55 g, 3.97 mmol). The mixture was heated at reflux for 16 h. After aqueous workup ($H_2O$/EtOAc or $H_2O$/$CH_2Cl_2$) the solvent was evaporated under reduced pressure and the crude product was purified by preparative HPLC to give compound Exemple E-1.

LC-MS $[M+H]^+$: 315.1; $t_R$=0.97 min*

*)Analytical UPLC column: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 mL/min in 1.50 minutes at 60° C.

C. Compound Examples

Compound example E-1 of the present invention is also shown in the synthesis examples above.

Examples of compounds of formula I according to the present invention are given in table E.1 below.

The Compound examples can be characterized e.g. by coupled High Performance Liquid Chromatography/mass spectrometry (HPLC/MS).

Analytical HPLC column: RP-18 column Chromolith Speed ROD from Merck KgaA, Germany).

Elution: acetonitrile+0.1% trifluoroacetic acid (TFA)/water+0.1% trifluoroacetic acid (TFA) in a ratio of from 5:95 to 95:5 in 5 minutes at 40° C.

MS-Method: ESI Positive.

General conditions: If not otherwise specified, most test solutions were or are to be prepared as follows: The active compound is to be dissolved at the desired concentration in a mixture of 1:1 (vol:vol) distilled water:acteon. Further, the test solutions are to be prepared at the day of use (and, if not otherwised specified, in general at concentrations wt/vol).

B.1 Green Peach Aphid (*Myzus persicae*)

For evaluating control of green peach aphid (*Myzus persicae*) through systemic means, the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

TABLE E.1

Examples of compounds according to formula I-E:

(I-E)

| No. | Het[a] | R[1] | R[2] | R[4] | X | R[3] | R[6] | Physico-chemical data[b] |
|-----|--------|------|------|------|---|------|------|--------------------------|
| E-1 | 5-chloro-2-pyridyl | H | H | H | O | CF3 | H | r.t. = 0.97 min* m/z = 315.1 |
| E-2 | 5-chloro-2-pyridyl | H | H | H | O | 4-methoxyphenyl | H | r.t. = 0.80 min* m/z = 353.2 |
| E-3 | 5-chloro-2-pyridyl | H | H | H | O | 3-pyridyl | H | r.t. = 0.58 min* m/z = 324.1 |
| E-4 | 5-chloro-2-pyridyl | H | H | H | O | 3-methylphenyl | H | r.t. = 0.79 min* m/z = 337.1 |
| E-5 | 5-chloro-2-pyridyl | H | H | H | O | 2-pyrazinyl | H | r.t. = 0.58 min* m/z = 343.0 |

[a] # denotes the attachment point to the remainder of the molecule;
[b] r.t. = HPLC retention time; m/z of the [M + H]+, [M + Na]+ or [M + K]+ peaks.
*analytical UPLC column (see above)

B. Biological Examples

The biological activity of the compounds of formula I of the present invention may be evaluated in biological tests as described in the following.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compounds E-1, E-3, E-4 and E-5 at 2500 ppm showed at least 75% mortality in comparison with untreated controls.

B.2 Cowpea Aphid (*Aphis craccivora*)

The active compound was dissolved at the desired concentration in a mixture of 1:1 (vol:vol) distilled water: acetone. Surfactant (Alkamuls® EL 620) was added at a rate of 0.1% (vol/vol). The test solution was prepared at the day of use.

Potted cowpea plants were colonized with approximately 50-100 aphids of various stages by manually transferring a leaf tissue cut from infested plant 24 hours before application. Plants were sprayed after the pest population has been recorded. Treated plants were maintained on light carts at about 28° C. Percent mortality was assessed after 72 hours.

In this test, compound E-1, E-3, and E-5 at 500 ppm showed at least 75% mortality in comparison with untreated controls.

B.3 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compound E-1, E-3, and E-5 at 2500 ppm showed at least 75% mortality in comparison with untreated controls.

B.4 Orchid *thrips* (*dichromothrips corbetti*)

*Dichromothrips corbetti* adults used for bioassay were obtained from a colony maintained continuously under laboratory conditions. For testing purposes, the test compound was diluted in a 1:1 mixture of acetone:water (vol:vol), plus 0.01% vol/vol Alkamuls® EL 620 surfactant.

*Thrips* potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with about 20 adult *thrips*. The petri dishes were then covered with lids. All test arenas were held under continuous light and a temperature of about 28° C. for duration of the assay. After 3 days, the numbers of live *thrips* were counted on each flower, and along inner walls of each petri dish. The percent mortality was recorded 72 hours after treatment.

In this test, compound E-1, and E-4 at 500 ppm showed at least 75% mortality in comparison with untreated controls.

B.5 Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) wss added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compound E-1, and E-5 at 500 ppm showed at least 75% mortality in comparison with untreated controls.

B.6 Rice Brown Plant Hopper (*Nilaparvata lugens*)

Rice seedlings were cleaned and washed 24 hours before spraying. The active compounds was formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compound E-1, and E-5 at 500 ppm showed at least 75% mortality in comparison with untreated controls.

B.7 Mediterranean Fruitfly (*Ceratitis capitata*)

For evaluating control of Mediterranean fruitfly (*Ceratitis capitata*) the test unit consists of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28±1° C. and about 80±5% relative humidity for 5 days. Egg and larval mortality was then visually assessed.

In this test, compound E-1, and E-5 at 2500 ppm showed at least 75% mortality in comparison with untreated controls.

Further biological assays, with which the biological activity of the compounds of formula I of the present invention may be assessed are described in the following.

B.8 Cotton Aphid (*Aphis gossypii*)

The active compounds are prepared and formulated in 50% acetone: 50% water (vol:vol) in glass vials.

Cotton seeds are placed in the glass vials and mixed with the formulated compounds. Solvent blank control seeds are treated with 50% acetone: 50% water (vol:vol). Treated seeds are then air-dried. The cotton seeds are planted in Metro Mix® potting mix in pots, 2 seeds per pot, and maintained in the greenhouse.

Seedling plants are thinned to one plant per pot. At the cotyledon stage, six plants are infested with *Aphis gossypii* by manually transferring circa 25 aphids to each plant on a piece of leaf tissue cut from a donor plant infested with aphids. Infested plants are maintained on light carts. Four days after infestation, live aphids on each plant are counted.

B.9 Silverleaf Whitefly (*Bemisia argentifolii*)

The active compounds are formulated in cyclohexanone as a 10,000 ppm solution supplied in tubes. The tubes are inserted into an automated electrostatic sprayer equipped with an atomizing nozzle and they serve as stock solutions for which lower dilutions are made in 50% acetone:50% water (v/v). A nonionic surfactant (Kinetic®) is included in the solution at a volume of 0.01% (v/v).

Cotton plants at the cotyledon stage (one plant per pot) are sprayed by an automated electrostatic plant sprayer equipped with an atomizing spray nozzle. The plants are dried in the sprayer fume hood and then removed from the sprayer. Each pot is placed into a plastic cup and about 10 to 12 whitefly adults (approximately 3-5 days old) are introduced. The insects are collected using an aspirator and a nontoxic Tygon® tubing connected to a barrier pipette tip. The tip, containing the collected insects, is then gently inserted into the soil containing the treated plant, allowing insects to crawl out of the tip to reach the foliage for feeding. Cups are covered with a reusable screened lid. Test plants are maintained in a growth room at about 25° C. and about 20-40% relative humidity for 3 days, avoiding direct exposure to fluorescent light (24 hour photoperiod) to prevent trapping of heat inside the cup. Mortality is assessed 3 days after treatment, compared to untreated control plants.

B.10 Boll Weevil (*Anthonomus grandis*)

For evaluating control of boll weevil (*Anthonomus grandis*) the test unit consist of 96-well-microtiter plates containing an insect diet and 5-10 *A. grandis* eggs.

The compounds are formulated using a solution containing 75% v/v water and 25% v/v DMSO. Different concentrations of formulated compounds are sprayed onto the insect diet at 5 μl, using a custom built micro atomizer, at two replications.

After application, microtiter plates are incubated at about 25±1° C. and about 75±5% relative humidity for 5 days. Egg and larval mortality is then visually assessed.

The invention claimed is:

1. A compound of formula (I):

(I)

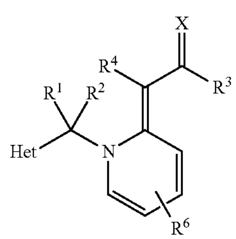

wherein

X is O, S, or $NR^5$;

Het is a 5 or 6 membered carbon-bound or optionally nitrogen-bound heterocyclic or heteroaromatic ring system, each ring member selected from carbon atoms and at least one, up to three heteroatoms independently selected from the group consisting of sulfur, oxygen and nitrogen, wherein the carbon, oxygen and nitrogen ring member can independently be partly or fully oxidized, and wherein each ring of the ring system is optionally substituted by k substituents selected from $R^{6a}$, wherein k is 1, 2, 3, 4, or 5, and two or more substituents $R^{6a}$ are selected independently from one another;

$R^1$ and $R^2$ are independently from each other selected from the group consisting of hydrogen, halogen, cyano, nitro, —SCN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-alkylthio, wherein each of the aforementioned carbon chain radicals are unsubstituted, partly or completely halogenated or may carry any combination of one or more radicals $R^7$, $Si(R^{11})_2R^{12}$, $OR^{16}$, $OSO_2R^{16}$, $S(O)_nR^{16}$, $S(O)_nNR^{17a}R^{17b}$; $NR^{17a}R^{17b}$; $C({=}O)NR^{17a}R^{17b}$, $C({=}S)NR^{17a}R^{17b}$, $C({=}O)OR^{16}$, $C({=}O)R^{15}$, $C({=}S)R^{15}$, phenyl, optionally substituted with one or more substituents $R^{18}$, which are independently selected from one another, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4, substituents $R^{18}$, selected independently from one another, and wherein the nitrogen and/or the sulfur atom(s) of the heterocyclic ring may optionally be oxidized, or $R^1$ and $R^2$ may together be ═O, ═$CR^{13}R^{14}$; ═S; ═$NR^{17a}$, ═$NOR^{16}$; ═$NNR^{17a}$;

$R^3$ is selected from the group consisting of hydrogen, halogen, cyano, SCN, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein each of the eight last mentioned carbon chain radicals are unsubstituted, partly or completely halogenated or may carry any combination of one or more radicals $R^7$;

$OR^8$, $OSO_2R^8$, $S(O)_nR^8$, $S(O)_nNR^{9a}R^{9b}$, $NR^{9a}R^{9b}$, $C({=}O)NR^{9a}R^{9b}$, $C({=}S)NR^{9a}R^{9b}$, $C({=}O)R^7$, $C({=}S)R^7$, phenyl, optionally substituted with one or more substituents $R^{10}$, which are independently selected from one another, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4 substituents $R^{18}$, selected independently from one another, and wherein the nitrogen and/or the sulfur atom(s) of the heterocyclic ring may optionally be oxidized;

$R^4$ is selected from the group consisting of hydrogen, halogen, cyano, nitro, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-alkylthio, wherein each of the six last mentioned carbon chain radicals are unsubstituted, partly or completely halogenated or may carry any combination of one or more radicals $R^7$, $Si(R^{11})_2R^{12}$, $OR^{16}$, $OSO_2R^{16}$, $S(O)_nR^{16}$, $S(O)_nNR^{17a}R^{17b}$, $NR^{17a}R^{17b}$, $C({=}O)NR^{17a}R^{17b}$, $C({=}S)NR^{17a}R^{17b}$, $C({=}O)OR^{16}$, $C({=}O)R^{15}$, $C({=}S)R^{15}$, phenyl, optionally substituted with 1, 2, 3, 4 or 5 substituents $R^{18}$, which are independently selected from one another, and a 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with one or more substituents $R^{10}$, selected independently from one another, and wherein the nitrogen and/or the sulfur atom(s) of the heterocyclic ring may optionally be oxidized;

$R^5$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals may be unsubstituted, partially or fully halogenated and/or oxygenated and/or may carry 1 or 2 radicals selected from $R^7$, phenyl, benzyl, pyridyl, and pyrimidyl, wherein the four last mentioned radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, $R^6$ and $R^{6a}$ are each, independently from the number of $R^6$ or $R^{6a}$ present and independently from one another, selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, and wherein the carbon atoms of the aforementioned aliphatic and cycloaliphatic radicals may optionally be further substituted independently from one another with one or more $R^7$, OR$^8$, NR$^{9a}$R$^{9b}$, S(O)$_n$R$^8$, S(O)$_n$NR$^{9a}$R$^{9b}$, C(=O)NR$^{9a}$R$^{9b}$, C(=O)OR$^8$, C(=S)R$^7$, C(=S)NR$^{9a}$R$^{9b}$, C(=S)OR$^8$, C(=S)SR$^8$, C(=NR$^{9a}$)R$^7$, C(=NR$^{9a}$)NR$^{9a}$R$^{9b}$, Si(R$^{11}$)$_2$R$^{12}$;

phenyl, optionally substituted with with 1, 2, 3, 4 or 5 substituents selected independently from R$^{10}$;

and a 3-, 4-, 5-, 6- or 7-membered saturated, partly saturated or unsaturated aromatic heterocyclic ring comprising 1, 2, 3 or 4 heteroatoms selected from oxygen, nitrogen and/or sulfur, optionally substituted with 1, 2, 3, 4 or 5 substituents selected independently from R$^{10}$, and wherein the nitrogen and/or the sulfur atom(s) of the heterocyclic ring may optionally be oxidized;

or two of R$^6$ or two of R$^{6a}$ present on one ring carbon or sulfur atom may together form =O, =CR$^{13}$R$^{14}$; =S; =NR$^{17a}$; =NOR$^{16}$; =NRR$^{17a}$;

R$^7$ is each independently from one another selected from the group consisting of hydrogen, halogen, cyano, azido, nitro, —SCN, SF$_5$, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, Si(R$^{11}$)$_2$R$^{12}$; OR$^{16}$; OSO$_2$R$^{16}$; S(O)$_n$ R$^{16}$, S(O)$_n$NR$^{17a}$R$^{17b}$, NR$^{17a}$R$^{17b}$, C(=O)NR$^{17a}$R$^{17b}$, C(=S)NR$^{17a}$R$^{17b}$, C(=O)OR$^{16}$, C(=O)R$^{15}$, C(=S)R$^{15}$, C(=NR$^{17a}$)R$^{15}$, phenyl, optionally substituted with 1, 2, 3, 4 or 5 substituents R$^{10}$, which are independently selected from one another, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4 substituents R$^{10}$, selected independently from one another, and wherein the nitrogen and/or the sulfur atom(s) of the heterocyclic ring may optionally be oxidized, or two R$^7$ present on one carbon atom may together form =O, =CR$^{13}$R$^{14}$; =S; =NR$^{17a}$, =NOR$^{16}$; =NNR$^{17a}$;

or two R$^7$ may form a 3-, 4-, 5-, 6-, 7- or 8-membered saturated or partly unsaturated carbocyclic or heterocyclic ring together with the carbon atoms to which the two R$^7$ are bonded to;

R$^8$ is each independently from one another selected from the group consisting of hydrogen, cyano, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, C$_3$-C$_8$-cycloalkyl, C$_4$-C$_8$-alkylcycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, Si(R$^{11}$)$_2$R$^{12}$, NR$^{17a}$R$^{17b}$, —N=CR$^{13}$R$^{14}$, —C(=O)R$^{15}$, C(=O)NR$^{17a}$R$^{17b}$), C(=S)NR$^{17a}$R$^{17b}$, C(=O)OR$^{16}$, phenyl, optionally substituted with one or more substituents R$^{10}$; which are selected independently from one another, and a 3-, 4-, 5-, 6- or 7-membered saturated or unsaturated aromatic heterocyclic ring comprising 1, 2 or 3 heteroatoms selected from oxygen, nitrogen and/or sulfur, optionally substituted with 1, 2, 3 or 4 substituents R$^{10}$, selected independently from one another, and wherein the nitrogen and/or the sulfur atom(s) of the heterocyclic ring may optionally be oxidized;

R$^{9a}$ and R$^{9b}$ are each independently from one another selected from the group consisting of hydrogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, S(O)$_n$R$^{16}$, —S(O)$_n$NR$^{17a}$R$^{17b}$, C(=O)R$^{15}$, C(=O)OR$^{16}$, C(=O)NR$^{17a}$R$^{17b}$, C(=S)R$^{15}$, C(=S)R$^{16}$, C(=S)NR$^{17a}$R$^{17b}$, C(=NR$^{17a}$)R$^{15}$;

phenyl, optionally substituted with one or more substituents R$^{10}$, which are selected independently from one another;

and a 3-, 4-, 5-, 6- or 7-membered saturated, partly saturated or unsaturated aromatic heterocyclic ring comprising 1, 2, 3 or 4 heteroatoms selected from oxygen, nitrogen and/or sulfur, optionally substituted with 1, 2, 3 or 4 substituents R$^{10}$, selected independently from one another, and wherein the nitrogen and/or the sulfur atom(s) of the heterocyclic ring may optionally be oxidized;

or,

R$^{9a}$ and R$^{9b}$ are together a C$_2$-C$_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteroatoms selected from oxygen, sulfur or nitrogen, and may optionally be substituted with halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, phenyl, optionally substituted with one or more substituents R$^{10}$; which are selected independently from one another, a 3-, 4-, 5-, 6-, or 7-membered saturated, partly saturated or unsaturated aromatic heterocyclic ring comprising 1, 2 or 3 heteroatoms selected from oxygen, nitrogen and/or sulfur, optionally substituted with one or more substituents R$^{10}$, selected independently from one another, and wherein the nitrogen and/or the sulfur atom(s) of the heterocyclic ring may optionally be oxidized;

or

R$^{9a}$ and R$^{9b}$ together may form a =CR$^{13}$R$^{14}$, =NR$^{17}$ or =NOR$^{16}$ radical;

R$^{10}$ is each independently from one another selected from the group consisting of hydrogen, halogen, cyano, azido, nitro, SCN, SF$_5$, C$_1$-C$_{10}$-alkyl, C$_3$-C$_8$-cycloalkyl, C$_2$-C$_{10}$-alkenyl, C$_2$-C$_{10}$-alkynyl, wherein the carbon atoms of the aforementioned aliphatic and cycloaliphatic radicals may optionally be substituted with one or more R$^{15}$, which are selected independently from one another, Si(R$^{11}$)$_2$R$^{12}$, OR$^{16}$, OS(O)$_n$R$^{16}$, —S(O)$_n$R$^{16}$, S(O$_n$NR$^{17a}$R$^{17b}$, NR$^{17a}$R$^{17b}$, C(=O)R$^{15}$, C(=S)R$^{15}$, C(=O)OR$^{16}$, —C(=NR$^{17a}$)R$^{15}$, C(=O)NR$^{17a}$R$^{17b}$, C(=S)NR$^{17a}$R$^{17b}$, phenyl, optionally substituted with halogen, cyano, nitro, C$_1$-C$_6$-alkyl, C$_1$-C$_6$-haloalkyl, C$_1$-C$_6$-alkoxy or C$_1$-C$_6$-haloalkoxy, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with one or more substituents selected independently from one another from halogen, cyano, NO$_2$, C$_1$-C$_6$-alkyl, C$_1$-C$_6$-haloalkyl, C$_1$-C$_6$-alkoxy or C$_1$-C$_6$-haloalkoxy, and wherein the nitrogen and/or the sulfur atom(s) of the heterocyclic ring may optionally be oxidized;

or two R$^{10}$ present together on one atom of a partly saturated heterocyclic may be =O, =CR$^{13}$R$^{14}$; =NR$^{17a}$, =NOR$^{16}$ or =NNR$^{17a}$;

or, two R$^{10}$ on adjacent carbon atoms may be a bridge selected from CH$_2$CH$_2$CH$_2$CH$_2$, CH=CH—CH=CH, N=CH—CH=CH, CH=N—CH=CH, N=CH—N=CH, OCH$_2$CH$_2$CH$_2$, OCH=CHCH$_2$, CH$_2$OCH$_2$CH$_2$, OCH$_2$CH$_2$O, OCH$_2$OCH$_2$, CH$_2$CH$_2$CH$_2$, CH=CHCH$_2$, CH$_2$CH$_2$O, CH=CHO, CH$_2$OCH$_2$, CH$_2$C(=O)O, C(=O)OCH$_2$, O(CH$_2$)O, SCH$_2$CH$_2$CH$_2$, SCH=CHCH$_2$, CH$_2$SCH$_2$CH$_2$, SCH$_2$CH$_2$S, SCH$_2$SCH$_2$, CH$_2$CH$_2$S, CH=CHS, CH$_2$SCH$_2$, CH$_2$C(=S)S, C(=S)SCH$_2$, S(CH$_2$)S, CH$_2$CH$_2$NR$^{17a}$, CH$_2$CH=N, CH=CH—NR$^{17a}$, OCH=N, SCH=N and form together with the carbon atoms to which the two R$^{10}$ are bonded to a 5-membered or 6-membered partly saturated or unsaturated, aromatic carbocyclic or heterocyclic ring, wherein the ring may optionally be substituted with one or two substituents selected from =O, OH, CH$_3$, OCH$_3$, halogen, cyano, halomethyl or halomethoxy;

R$^{11}$ and R$^{12}$ are each independently from one another selected from the group consisting of hydrogen, halogen, C$_1$-C$_6$ alkyl, C$_1$-C$_6$ haloalkyl, C$_1$-C$_6$ alkoxy, C$_1$-C$_6$ alkoxyalkyl, C$_2$-C$_6$ alkenyl, C$_2$-C$_6$ haloalkenyl, C$_2$-C$_6$-alkynyl, C$_2$-C$_6$-haloalkynyl, C$_3$-C$_8$ cycloalkyl, C$_3$-C$_8$ halocycloalkyl, C$_1$-C$_6$ alkoxyalkyl, C$_1$-C$_6$ haloalkoxyalkyl and phenyl, optionally substituted with one or more substituents R$^{18}$; which are selected independently from one another;

R$^{13}$ and R$^{14}$ are each independently from one another selected from the group consisting of hydrogen, C$_1$-C$_4$ alkyl, C$_3$-C$_6$-cycloalkyl, C$_1$-C$_4$ alkoxyalkyl, phenyl and benzyl;

R$^{15}$ is each independently from one another selected from the group consisting of hydrogen, halogen, cyano, nitro, OH, SH, SCN, SF$_5$, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tertbutyldimethylsilyl, C$_1$-C$_6$-alkyl, C$_2$-C$_6$-alkenyl, C$_2$-C$_6$-alkynyl, C$_3$-C$_8$-cycloalkyl, wherein the four last mentioned aliphatic and cycloaliphatic radicals may be unsubstituted, partially or fully halogenated and/or oxygenated and/or may carry 1 or 2 radicals selected from C$_1$-C$_4$ alkoxy;

phenyl, benzyl, pyridyl, and phenoxy, wherein the last four radicals may be unsubstituted, partially or fully halogenated and/or to carry 1, 2 or 3 substituents selected from the group consisting of C$_1$-C$_6$-alkyl, C$_1$-C$_6$-haloalkyl, C$_1$-C$_6$-alkoxy, C$_1$-C$_6$ haloalkoxy, (C$_1$-C$_6$-alkoxy)carbonyl, (C$_1$-C$_6$-alkyl)amino and di-(C$_1$-C$_6$-alkyl)amino, or two R$^{15}$ present on the same carbon atom may together be =O, =CH(C$_1$-C$_4$), =C(C$_1$-C$_4$-alkyl)C$_1$-C$_4$-alkyl, =N(C$_1$-C$_6$-alkyl) or =NO(C$_1$-C$_6$-alkyl);

R$^{16}$ is each independently from one another selected from the group consisting of hydrogen, cyano, C$_1$-C$_6$-alkoxy, C$_1$-C$_6$-haloalkoxy, C$_1$-C$_6$-alkylsulfinyl, C$_1$-C$_6$-alkylsulfonyl, C$_1$-C$_6$-haloalkylthio, trimethylsilyl, triethylsilyl, tertbutyldimethylsilyl, C$_1$-C$_6$-alkyl, C$_2$-C$_6$-alkenyl, C$_2$-C$_6$-alkynyl, C$_3$-C$_8$-cycloalkyl, wherein the four last mentioned radicals may be unsubstituted, partially or fully halogenated and/or oxygenated and/or may carry 1 or 2 radicals selected from C$_1$-C$_4$ alkoxy, phenyl, benzyl, pyridyl, and phenoxy, wherein the last four radicals may be unsubstituted, partially or fully halogenated and/or carry 1, 2 or 3 substituents selected from C$_1$-C$_6$-alkyl, C$_1$-C$_6$-haloalkyl, C$_1$-C$_6$-alkoxy, C$_1$-C$_6$-haloalkoxy or (C$_1$-C$_6$-alkoxy)carbonyl;

R$^{17a}$ and R$^{17b}$ are each independently from one another selected from the group consisting of hydrogen, cyano, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tertbutyldimethylsilyl, C$_1$-C$_6$-alkyl, C$_2$-C$_6$-alkenyl, C$_2$-C$_6$-alkynyl, C$_3$-C$_8$-cycloalkyl, wherein the four last mentioned aliphatic and cycloaliphatic radicals may be unsubstituted, partially or fully halogenated and/or oxygenated and/or may carry 1 or 2 radicals selected from C$_1$-C$_4$-alkoxy, phenyl, benzyl, pyridyl, phenoxy, wherein the four last mentioned radicals may be unsubstituted, partially or fully halogenated and/or carry 1, 2 or 3 substituents selected from C$_1$-C$_6$-alkyl, C$_1$-C$_6$-alkoxy, C$_1$-C$_6$ haloalkoxy or (C$_1$-C$_6$-alkoxy)carbonyl, or, R$^{17a}$ and R$^{17b}$ may together be a C$_2$-C$_6$ alkylene chain forming a 3- to 7-membered saturated, partly saturated or unsaturated ring together with the nitrogen atom R$^{17a}$ and R$^{17b}$ are bonded to, wherein the alkylene chain may contain 1 or 2 heteroatoms selected from oxygen, sulfur or nitrogen, and may optionally be substituted with halogen, C$_1$-C$_4$-haloalkyl, C$_1$-C$_4$-alkoxy or C$_1$-C$_4$-haloalkoxy, and wherein the nitrogen and/or the sulfur atom(s) of the heterocyclic ring may optionally be oxidized;

n is independently from one another 0, 1 or 2;

and/or an enantiomer, diastereomer, E/Z-isomer or agriculturally or veterinarily acceptable salt thereof.

2. The compound of claim 1, wherein

Het is selected from the group consisting of Het-1, Het-2, Het-3, Het-4, Het-5, Het-6, Het-7, Het-8, Het-9, Het-10, Het-11, Het-12, Het-13, Het-14, Het-15, Het-16, Het-17, Het-18, Het-19, Het-20, Het-21, Het-22, Het-23, and Het-24:

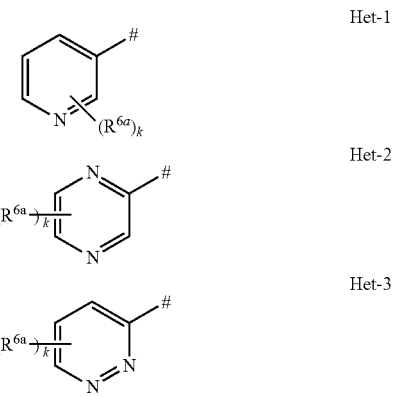

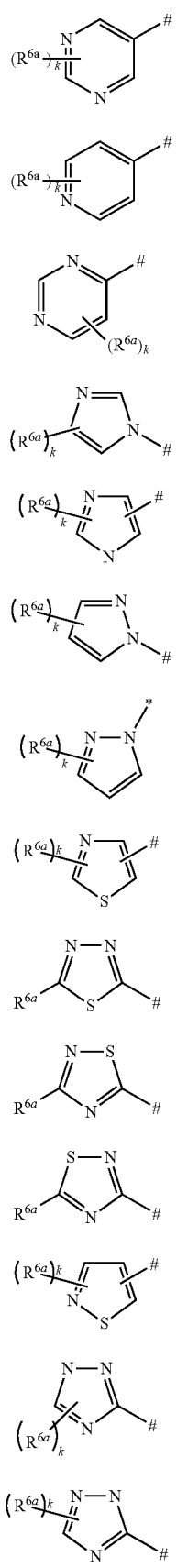
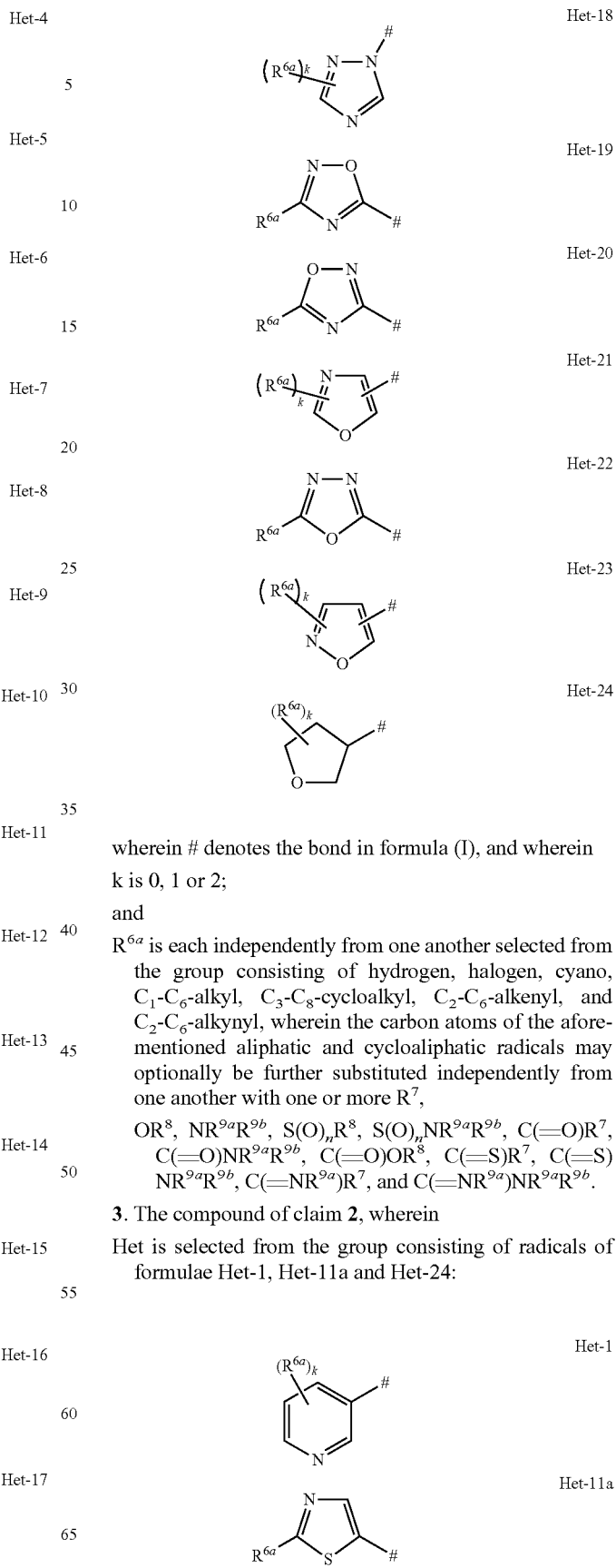

wherein # denotes the bond in formula (I), and wherein k is 0, 1 or 2;

and $R^{6a}$ is each independently from one another selected from the group consisting of hydrogen, halogen, cyano, $C_1$-$C_6$-alkyl, $C_3$-$C_8$-cycloalkyl, $C_2$-$C_6$-alkenyl, and $C_2$-$C_6$-alkynyl, wherein the carbon atoms of the aforementioned aliphatic and cycloaliphatic radicals may optionally be further substituted independently from one another with one or more $R^7$, $OR^8$, $NR^{9a}R^{9b}$, $S(O)_n R^8$, $S(O)_n NR^{9a}R^{9b}$, $C(=O)R^7$, $C(=O)NR^{9a}R^{9b}$, $C(=O)OR^8$, $C(=S)R^7$, $C(=S)NR^{9a}R^{9b}$, $C(=NR^{9a})R^7$, and $C(=NR^{9a})NR^{9a}R^{9b}$.

3. The compound of claim 2, wherein

Het is selected from the group consisting of radicals of formulae Het-1, Het-11a and Het-24:

-continued

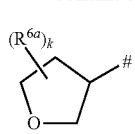
Het-24 wherein # denotes the bond in formula (I), and wherein
$R^{6a}$ is selected from hydrogen, halogen, $C_1$-$C_4$-alkoxy or $C_1$-$C_4$-alkyl, wherein the carbon atoms of the latter two radicals may be partially of fully halogenated; and k is 0, 1 or 2.

4. The compound of claim 1, wherein
$R^1$ and $R^2$ are independently from each other selected from the group consisting of hydrogen, halogen, cyano, $C_1$-$C_6$-alkyl, $C_3$-$C_6$-cycloalkyl, $C_1$-$C_6$-haloalkyl, $C_3$-$C_6$-halocycloalkyl; or
$R^1$ and $R^2$ may together be =O, =$CR^{13}R^{14}$ or =S; or
$R^1$ and $R^2$ form, together with the carbon atom, which they attached to, a 3- to 5-membered saturated carbocyclic ring.

5. The compound claim 1, wherein
$R^3$ is hydrogen, halogen, cyano, SCN, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_8$-cycloalkyl, $C_2$-$C_6$-alkenyl, $C_2$-$C_6$-alkynyl, wherein each of the eight last mentioned radicals are unsubstituted, partly or completely halogenated or may carry any combination of one or more radicals $R^7$,
$OR^8$, $S(O)_n R^8$, $NR^{9a}R^{9b}$,
phenyl, optionally substituted with 1, 2, 3, 4 or 5 substituents $R^{10}$, which are independently selected from one another,
or a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with 1, 2, 3 or 4, substituents $R^{18}$, selected independently from one another, and wherein the nitrogen and/or the sulfur atom(s) of the heterocyclic ring may optionally be oxidized.

6. The compound of claim 1, wherein
$R^4$ is hydrogen, halogen, cyano, nitro, $C_1$-$C_4$-alkyl, $C_3$-$C_6$-cycloalkyl, $C_1$-$C_4$-alkoxy, or $C_1$-$C_4$-alkylthio, wherein each of the four last mentioned radicals are unsubstituted, partly or completely halogenated or may carry any combination of one or more radicals $R^7$.

7. The compound of claim 1, wherein
X is O, S, or $NR^5$; and wherein
$R^5$ is hydrogen, cyano, $C_1$-$C_6$-alkyl, $C_1$-$C_6$-alkoxy, $C_1$-$C_6$-alkylthio, or $C_3$-$C_8$-cycloalkyl, wherein each of the four last mentioned radicals are unsubstituted, partly or completely halogenated or may carry any combination of one or more radicals $R^7$.

8. The compound of claim 1, wherein
$R^6$ is each independently from one another selected from the group consisting of hydrogen, halogen, cyano, $C_1$-$C_{10}$-alkyl, $C_3$-$C_8$-cycloalkyl, $C_2$-$C_{10}$-alkenyl, $C_{10}$-alkynyl, wherein the carbon atoms of the aforementioned aliphatic and cycloaliphatic radicals may optionally be further substituted independently from one another with one or more $R^7$,
$OR^B$, $NR^{9a}R^{9b}$, $S(O)_n R^8$, $S(O)_n NR^{9a}R^{9b}$, $C(=O)R^7$, $C(=O)NR^{9a}R^{9b}$, $C(=O)OR^8$, $C(=S)R^7$, $C(=S)NR^{9a}R^{9b}$, $C(=NR^{9a})R^7$, and $C(=NR^{9a})NR^{9a}R^{9b}$.

9. The compound of claim 1, wherein
Het is selected from the group consisting of Het-1, Het-11a and Het-24

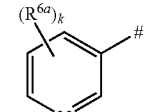
Het-1

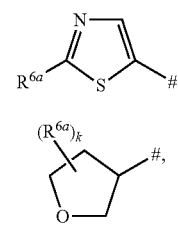
Het-11a

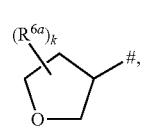
Het-24 wherein # denotes the bond in formula (I), and wherein
$R^{6a}$ is selected from hydrogen, halogen, $C_1$-$C_4$-alkoxy or $C_1$-$C_4$-alkyl, wherein the carbon atoms of the latter two radicals may be partially of fully halogenated;
k is 0, 1 or 2;
X is O or S;
$R^1$ and $R^2$ are independently from each other selected from the group consisting of hydrogen, halogen, cyano, $C_1$-$C_3$-alkyl, and $C_1$-$C_3$-haloalkyl;
$R^4$ is selected from the group consisting of hydrogen, halogen, cyano, nitro, $C_1$-$C_4$-cycloalkyl, $C_3$-$C_6$-alkoxy, and $C_1$-$C_4$-alkylthio, wherein
each of the four last mentioned radicals are unsubstituted, partly or completely halogenated;
and
$R^6$ is hydrogen, halogen, cyano, $C_1$-$C_4$-alkoxy or $C_1$-$C_4$-alkyl, wherein the carbon atoms of the latter two radicals may be partially of fully halogenated.

10. The compound of claim 1, wherein
Het is

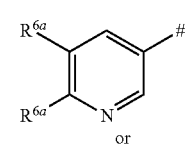
Het-1 or

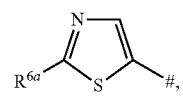
Het-11a wherein # denotes the bond in formula (I), and wherein
$R^{6a}$ is hydrogen, halogen or $C_1$-$C_4$-haloalkyl;
X is from O or S;
$R^1$ and $R^2$ are both hydrogen;
$R^3$ is hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl,
$OR^{15}$, $S(O)_n R^{16}$, $NR^{17a}R^{17b}$, phenyl, optionally substituted with one or more substituents R¹⁰, which are independently selected from one another, or a 5- or 6-membered heteroaromatic ring comprising 1, 2 or 3 heteroatoms selected from oxygen, nitrogen and/or sulfur, optionally substituted with one or more substituents R¹⁰, selected independently from one another, and wherein the nitrogen and/or the sulfur atom(s) of the heterocyclic ring may optionally be oxidized;

R⁴ is selected from the group consisting of hydrogen, halogen, cyano, $C_1$-$C_4$-alkyl, $C_3$-$C_6$-cycloalkyl, $C_1$-$C_4$-alkoxy, and $C_1$-$C_4$-alkylthio, wherein each of the four last mentioned radicals are unsubstituted, partly or completely halogenated;

and

R⁶ is selected from hydrogen, halogen, cyano, $C_1$-$C_4$-alkoxy and $C_1$-$C_4$-alkyl, wherein the carbon atoms of the latter two radicals may be partially of fully halogenated.

11. An agricultural or veterinary composition comprising a compound of claim 1 and at least one agriculturally or veterinarily acceptable carrier and optionally, if desired, at least one surfactant.

12. A method for combating or controlling insects, arachnids or nematodes, which method comprises contacting said insects, arachnids or nematodes or their food supply, habitat or breeding grounds with a pesticidally effective amount of a compound of claim 1.

13. The method of claim 12, wherein Het is selected from the group consisting of Het-1, Het-2, Het-3, Het-4, Het-5, Het-6, Het-7, Het-8, Het-9, Het-10, Het-11, Het-12, Het-13, Het-14, Het-15, Het-16, Het-17, Het-18, Het-19, Het-20, Het-21, Het-22, Het-23, and Het-24:

-continued

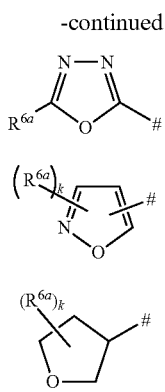

Het-22

Het-23

Het-24 wherein # denotes the bond in formula (I), and wherein
k is 0, 1 or 2;
and
$R^{6a}$ is each independently from one another selected from
the group consisting of hydrogen, halogen, cyano,
$C_1$-$C_6$-alkyl, $C_3$-$C_8$-cycloalkyl, $C_2$-$C_6$-alkenyl, and
$C_2$-$C_6$-alkynyl, wherein the carbon atoms of the aforementioned aliphatic and cycloaliphatic radicals may
optionally be further substituted independently from
one another with one or more $R^7$,
$OR^8$, $NR^{9a}R^{9b}$, $S(O)_nR^8$, $S(O)_nNR^{9a}R^{9b}$, $C(=O)R^7$,
$C(=O)NR^{9a}R^{9b}$, $C(=O)OR^8$, $C(=S)R^7$, $C(=S)$
$NR^{9a}R^{9b}$, $C(=NR^{9a})R^7$, and $C(=NR^{9a})NR^{9a}R^{9b}$.

14. The method of claim 13, wherein Het is selected from
the group consisting of Het-1, Het-11a and Het-24:

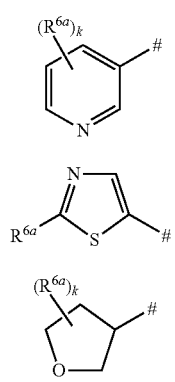

Het-1

Het-11a

Het-24 wherein # denotes the bond in formula (I), and wherein
$R^{6a}$ is selected from hydrogen, halogen, $C_1$-$C_4$-alkoxy
or $C_1$-$C_4$-alkyl, wherein the carbon atoms of the latter
two radicals may be partially of fully halogenated;
and k is 0, 1 or 2.

15. The method of claim 12, wherein
$R^1$ and $R^2$ are independently from each other selected from
the group consisting of hydrogen, halogen, cyano,
$C_1$-$C_6$-alkyl, $C_3$-$C_6$-cycloalkyl, $C_1$-$C_6$-haloalkyl, and
$C_3$-$C_6$-halocycloalkyl; or
$R^1$ and $R^2$ may together be =O, =$CR^{13}R^{14}$ or =S; or
$R^1$ and $R^2$ form, together with the carbon atom, which
they attached to, a 3- to 5-membered saturated carbocyclic ring.

16. The method of claim 12, wherein $R^3$ is hydrogen,
halogen, cyano, SCN, $C_1$-$C_6$-alkoxy, $C_1$-$C_6$-alkylthio,
$C_1$-$C_6$-alkylsulfinyl, $C_1$-$C_6$-alkylsulfonyl, $C_3$-$C_8$-cycloalkyl,
$C_2$-$C_6$-alkenyl, $C_2$-$C_6$-alkynyl, wherein each of the eight last
mentioned radicals are unsubstituted, partly or completely
halogenated or may carry any combination of one or more
radicals $R^7$,
$OR^8$, $S(O)_nR^8$, $NR^{9a}R^{9b}$,
phenyl, optionally substituted with 1, 2, 3, 4 or 5 substituents $R^{10}$, which are independently selected from one
another,
and a 3-, 4-, 5-, 6- or 7-membered saturated, partly saturated or unsaturated aromatic heterocyclic ring comprising 1, 2 or 3 heteroatoms selected from oxygen, nitrogen
and/or sulfur, optionally substituted with 1, 2, 3 or 4,
substituents $R^{18}$, selected independently from one
another, and wherein the nitrogen and/or the sulfur atom
(s) of the heterocyclic ring may optionally be oxidized.

17. The method of claim 12, wherein $R^4$ is hydrogen,
halogen, cyano, nitro, $C_1$-$C_4$-alkyl, $C_3$-$C_6$-cycloalkyl, $C_1$-$C_4$-alkoxy, or $C_1$-$C_4$-alkylthio, wherein each of the four last
mentioned radicals are unsubstituted, partly or completely
halogenated or may carry any combination of one or more
radicals $R^7$.

18. The method of claim 12, wherein X is O, S, or $NR^5$; and
wherein, $R^5$ is
hydrogen, cyano, $C_1$-$C_6$-alkoxy, $C_1$-$C_6$-alkylthio, and
$C_3$-$C_8$-cycloalkyl, wherein each of the four last mentioned radicals are unsubstituted, partly or completely
halogenated or may carry any combination of one or
more radicals $R^7$.

19. The method of claim 12, wherein
$R^6$ is each independently from one another selected from
the group consisting of hydrogen, halogen, cyano,
$C_3$-$C_8$-cycloalkyl, $C_2$-$C_{10}$-alkenyl, $C_2$-$C_{10}$-alkynyl, and
wherein the carbon atoms of the aforementioned aliphatic and cycloaliphatic radicals may optionally be
further substituted independently from one another with
one or more $R^7$,
$OR^8$, $NR^{9a}R^{9b}$, $S(O)_nR^8$, $S(O)_nNR^{9a}R^{9b}$, $C(=O)R^7$,
$C(=O)NR^{9a}R^{9b}$, $C(=O)OR^8$, $C(=S)R^7$, $C(=S)$
$NR^{9a}R^{9b}$, $C(=NR^{9a})R^7$, and $C(=NR^{9a})NR^{9a}R^{9b}$.

20. The method of claim 12, wherein Het is selected from
the group consisting of Het-1, Het-11a and Het-24

Het-1

Het-11a

Het-24 wherein # denotes the bond in formula (I), and wherein
$R^{6a}$ is selected from hydrogen, halogen, $C_1$-$C_4$-alkoxy or
$C_1$-$C_4$-alkyl, wherein the carbon atoms of the latter two
radicals may be partially of fully halogenated;
k is 0, 1 or 2;
X is O or S;

$R^1$ and $R^2$ are independently from each other selected from the group consisting of hydrogen, halogen, cyano, $C_1$-$C_3$-alkyl, or $C_1$-$C_3$-haloalkyl;

$R^4$ is selected from the group consisting of hydrogen, halogen, cyano, nitro, $C_3$-$C_6$-cycloalkyl, $C_1$-$C_4$-alkoxy, $C_1$-$C_4$-alkylthio, wherein each of the four last mentioned radicals are unsubstituted, partly or completely halogenated;

and $R^6$ is selected from hydrogen, halogen, cyano, $C_1$-$C_4$-alkoxy and $C_1$-$C_4$-alkyl, wherein the carbon atoms of the latter two radicals may be partially of fully halogenated.

21. The method of claim 12, wherein Het is

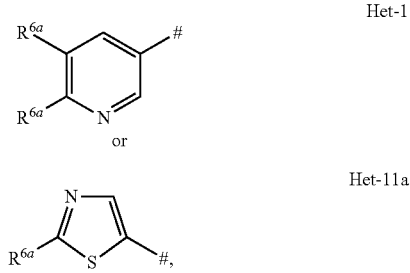

wherein # denotes the bond in formula (I), and wherein $R^{6a}$ is hydrogen, halogen or $C_1$-$C_4$-haloalkyl;
X is O or S;
$R^1$ and $R^2$ are both hydrogen;
$R^3$ is selected from the group consisting of hydrogen, cyano, $C_1$-$C_6$-alkyl, $C_1$-$C_6$-halo alkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $OR^{15}$, $S(O)_nR^{16}$, $NR^{17a}R^{17b}$, phenyl, optionally substituted with one or more substituents $R^{10}$, which are independently selected from one another, or a 5- or 6-membered heteroaromatic ring comprising 1, 2 or 3 heteroatoms selected from oxygen, nitrogen and/or sulfur, optionally substituted with one or more substituents $R^{10}$, selected independently from one another, and wherein the nitrogen and/or the sulfur atom(s) of the heterocyclic ring may optionally be oxidized;

$R^4$ is selected from the group consisting of hydrogen, halogen, cyano, $C_1$-$C_4$-alkyl, $C_3$-$C_6$-cycloalkyl, $C_1$-$C_4$-alkoxy, and $C_1$-$C_4$-alkylthio, wherein each of the four last mentioned radicals are unsubstituted, partly or completely halogenated;

and $R^6$ is selected from hydrogen, halogen, cyano, $C_1$-$C_4$-alkoxy and $C_1$-$C_4$-alkyl, wherein the carbon atoms of the latter two radicals may be partially of fully halogenated.

22. A method for protecting growing plants from attack or infestation by insects, arachnids or nematodes, which method comprises contacting said growing plants, or the soil or water of said growing plants, with a pesticidally effective amount of a compound of claim 1.

23. A method for protecting seeds, seedling roots and shoots from soil and foliar insects, which method comprises contacting said seeds, seedling roots and shoots with a pesticidally effective amount of a compound of claim 1.

24. A method for treating or preventing animal infestation or infection by parasites or protecting an animal against infestation or infection by parasites, which method comprises administering or applying to said animal a parasitically effective amount of a compound of claim 1.

* * * * *